(12) United States Patent
Kwak et al.

(10) Patent No.: US 9,163,004 B2
(45) Date of Patent: *Oct. 20, 2015

(54) ORGANIC LIGHT-EMITTING DEVICE

(75) Inventors: Yoon-Hyun Kwak, Yongin (KR); Seok-Hwan Hwang, Yongin (KR); Young-Kook Kim, Yongin (KR); Hye-Jin Jung, Yongin (KR); Jong-Hyuk Lee, Yongin (KR); Hee-Joo Ko, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 770 days.

This patent is subject to a terminal disclaimer.

(21) Appl. No.: 13/164,348

(22) Filed: Jun. 20, 2011

(65) Prior Publication Data

US 2011/0309348 A1    Dec. 22, 2011

(30) Foreign Application Priority Data

Jun. 21, 2010 (KR) .................. 10-2010-0058622

(51) Int. Cl.
*H01L 51/52* (2006.01)
*C07D 209/58* (2006.01)
(Continued)

(52) U.S. Cl.
CPC ............ *C07D 401/14* (2013.01); *C07D 209/08* (2013.01); *C07D 209/60* (2013.01);
(Continued)

(58) Field of Classification Search
CPC .. C07D 209/08; C07D 401/14; C07D 413/10; C07D 487/04; H01L 51/0067; H01L 51/0081; H01L 2251/308
See application file for complete search history.

(56) References Cited

U.S. PATENT DOCUMENTS 5,645,948 A    7/1997 Shi et al.
8,399,880 B2 *  3/2013 Kim et al. .................. 257/40
(Continued)

FOREIGN PATENT DOCUMENTS

JP    11-144866      5/1999
JP    2005-093159 A  4/2005
(Continued)

OTHER PUBLICATIONS

Rawal et al., Tetrahedron Letters, (1985), vol. 26, No. 20, pp. 2423-2426.*

(Continued)

*Primary Examiner* — Dawn Garrett
(74) *Attorney, Agent, or Firm* — Knobbe Martens Olson & Bear LLP

(57) ABSTRACT

A heterocyclic compound represented by Formula 1 below and an organic light-emitting device including the heterocyclic compound:

Formula 1

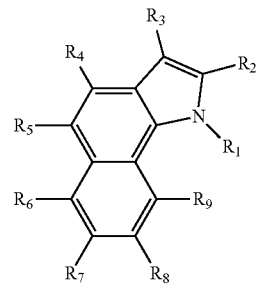

wherein $R_1$ through $R_9$ are defined as in the specification.

16 Claims, 1 Drawing Sheet

(51) Int. Cl.
  *C07D 235/02* (2006.01)
  *C07D 263/60* (2006.01)
  *C07D 401/14* (2006.01)
  *C07D 209/08* (2006.01)
  *C07D 209/60* (2006.01)
  *C07D 403/10* (2006.01)
  *C07D 413/10* (2006.01)
  *C07D 471/04* (2006.01)
  *C07D 487/04* (2006.01)
  *C07D 519/00* (2006.01)
  *H01L 51/00* (2006.01)
  *H01L 51/50* (2006.01)

(52) U.S. Cl.
  CPC ............ *C07D403/10* (2013.01); *C07D 413/10* (2013.01); *C07D 471/04* (2013.01); *C07D 487/04* (2013.01); *C07D 519/00* (2013.01); *H01L 51/0067* (2013.01); *H01L 51/0072* (2013.01); *H01L 51/0081* (2013.01); *H01L 51/5072* (2013.01); *H01L 2251/308* (2013.01)

(56) References Cited

U.S. PATENT DOCUMENTS

| | | | |
|---|---|---|---|
| 2004/0076853 A1* | 4/2004 | Jarikov | 428/690 |
| 2006/0086938 A1* | 4/2006 | Kang et al. | 257/72 |
| 2006/0115680 A1 | 6/2006 | Hwang et al. | |
| 2009/0096356 A1* | 4/2009 | Murase et al. | 313/504 |
| 2010/0075260 A1* | 3/2010 | Sasaki | 430/302 |
| 2011/0049487 A1* | 3/2011 | Kim et al. | 257/40 |
| 2011/0049494 A1 | 3/2011 | Kim et al. | |

FOREIGN PATENT DOCUMENTS

| | | |
|---|---|---|
| JP | 2008-133225 A | 6/2008 |
| JP | 2011-219473 A | 11/2011 |
| JP | 5258846 B2 | 8/2013 |
| KR | 10-2006-0059613 A | 6/2006 |
| KR | 10-2006-0069442 A | 6/2006 |
| KR | 10-2008-0096733 A | 11/2008 |
| KR | 10-2011-0023090 A | 3/2011 |
| WO | WO 03/059014 A1 | 7/2003 |
| WO | WO 2004/101767 A2 | 11/2004 |
| WO | WO 2010/021524 A2 * | 2/2010 |

OTHER PUBLICATIONS

Chem. Eur. J. (2010), vol. 16, pp. 11707-11711.*
Organic Letters, (2010), 12(23). p. 5426-5429.*
Katritzky et al., Journal of Heterocyclic Chemistry, (1986), 23(3), pp. 865-870.*
Jose Barluenga, Agustin Jimenez-Aquino, Fernando Aznar and Carlos Valdes, Modular Synthesis of Indoles from Imines and o-Dihaloarenes or o-Chlorosulfonates by a Pd-Catalyzed Cascade Process, Journal Abstract, 2009, 131 (11), American Chemical Society.
E.E. Baroni and K.A. Kovyrzina, Indole derivatives, Journal Abstract, 1959, vol. 29, Zhurnal Obshchei Khimii.
Korean Official Action issued by the Korean Industrial Property Office dated Mar. 26, 2012 in examination of Korean Patent Application No. 10-2010-0058622, 6 pages.
Registration Determination Certificate issued by the Korean Intellectual Property Office dated Oct. 31, 2012, 5 pages.
Office Action dated May 19, 2015, issued in corresponding Japanese Patent Application No. 2011-111515.
Petkova et al., Structure of Photophysics of 2-(2'-Pyridyl)benzidoles: The Role of Intermolecular Hydrogen Bonds, Journal of Physical Chemistry A 2007, vol. 111, pp. 11400-11409.
Salituro et al., 3-(2-Carboxyindol-3-yl)propionic Acid-Based Antagonists of the N-Methyl-D-aspartic Acid Receptor Associated Glycine Binding Site, Journal of Medicinal Chemistry, 1992, vol. 35 No. 10, pp. 1791-1799.
Fujiwara et al. Nucleophilic Aromatic Substitution by Organoaluminum Reagents. Application to the Synthesis of Indoles. Journal of the American Chemical Society, 1983, vol. 105, No. 24. pp. 7177-7179.
Richards, Preparation of Substituted Indoles from Benzoin and Secondary Arylamines, Journal of the Chemical Society, Transactions, 1910, vol. 97,pp. 977-980.

* cited by examiner

| SECOND ELECTRODE |
|---|
| ELECTRON INJECTION LAYER |
| ELECTRON TRANSPORT LAYER |
| EMISSION LAYER |
| HOLE TRANSPORT LAYER |
| HOLE INJECTION LAYER |
| FIRST ELECTRODE |

ORGANIC LIGHT-EMITTING DEVICE

CROSS-REFERENCE TO RELATED APPLICATIONS

This application claims the benefit of Korean Patent Application No. 10-2010-0058622, filed on Jun. 21, 2010, in the Korean Intellectual Property Office, the disclosure of which is incorporated herein in its entirety by reference.

BACKGROUND

1. Field

The present embodiments relate to a heterocyclic compound represented by Formula 1 and an organic light-emitting device including the heterocyclic compound.

2. Description of the Related Technology

Organic light-emitting devices are self-emitting display devices and have wide viewing angles, high contrast ratios, and short response times. Due to these characteristics, organic light-emitting devices are drawing more attention.

Such light-emitting devices can be roughly classified into inorganic light-emitting devices that include emission layers containing inorganic compounds, and organic light-emitting devices that include emission layers containing organic compounds. Specifically, organic light-emitting devices have higher luminance, lower driving voltages, and shorter response times than inorganic light-emitting devices, and can render multi-colored displays. Thus, much research into such organic light-emitting devices has been conducted.

Typically, an organic light-emitting device has a stack structure including an anode, a cathode and an organic emission layer between the anode and the cathode. However, a hole injection layer and/or a hole transport layer may be further stacked between the anode and the organic emission layer, and/or an electron transport layer may be further stacked between the organic emission layer and the cathode. An organic light-emitting device may have an anode/hole transport layer/organic emission layer/cathode structure or an anode/hole transport layer/organic emission layer/electron transport layer/cathode structure.

As a material for the organic emission layer, a phenanthrene derivative may be used. However, organic light-emitting devices including such as known organic emission materials do not have satisfactory life span, efficiency, and power consumption characteristics.

SUMMARY

The present embodiments provide a heterocyclic compound having improved electrical characteristics, charge transporting capabilities and light-emission capabilities.

The present embodiments provide an organic light-emitting device including the heterocyclic compound.

The present embodiments provide a flat panel display device including the organic light-emitting device.

The present embodiments provide an organic light-emitting device including at least one layer containing the heterocyclic compound, wherein the at least one layer is formed using a wet process.

According to an aspect of the present embodiments, there is provided a heterocyclic compound represented by Formula 1 below:

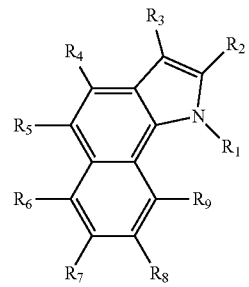

Formula 1 wherein $R_1$ through $R_9$ may be each independently a hydrogen atom, a heavy hydrogen atom, a substituted or unsubstituted $C_1$-$C_{50}$ alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a substituted or unsubstituted $C_5$-$C_{60}$ aryl group, a substituted amino group with a $R_5$-$R_{60}$ aryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group, wherein two vicinal substituents among $R_1$ through $R_9$ may be linked to each other to form an aromatic ring.

$R_1$, $R_2$, $R_3$ or $R_6$ may be an aryl group.

$R_6$ may be an unsubstituted monocyclic to tetracyclic aryl group selected from the group consisting of a phenyl group, a naphthyl group, a biphenyl group, a terphenyl group, an anthracenyl group, a fluorenyl group, a carbazolyl group, and a pyrenyl group; an unsubstituted $C_3$-$C_{60}$ heteroaryl group; an unsubstituted $C_5$-$C_{50}$ arylamine group; a substituted monocyclic to tetracyclic aryl group selected from the group consisting of a phenyl group, a naphthyl group, a biphenyl group, a terphenyl group, an anthracenyl group, a fluorenyl group, a carbazolyl group, and a pyrenyl group which are optionally substituted with a $C_1$-$C_5$ alkyl group, a $C_1$-$C_5$ alkoxy group, a cyano group, an amine group, a phenoxy group, a phenyl group or a halogen group; a substituted $C_3$-$C_{60}$ heteroaryl group which is optionally substituted with a $C_1$-$C_5$ alkyl group, a $C_1$-$C_5$ alkoxy group, a cyano group, an amine group, a phenoxy group, a phenyl group, a halogen group or a $C_3$-$C_{10}$ heteroaryl group; or a substituted $C_5$-$C_{50}$ arylamine group which is substututed with a $C_1$-$C_5$ alkyl group, a $C_1$-$C_5$ alkoxy group, a cyano group, an amine group, a phenoxy group, a phenyl group or a halogen group.

$R_1$ may be an unsubstituted monocyclic to tetracyclic aryl group selected from the group consisting of a phenyl group, a naphthyl group, a biphenyl group, a terphenyl group, an anthracenyl group, a fluorenyl group, a carbazolyl group, and a pyrenyl group; an unsubstituted $C_3$-$C_{60}$ heteroaryl group; a substituted monocyclic to tetracyclic aryl group selected from the group consisting of a phenyl group, a naphthyl group, a biphenyl group, a terphenyl group, an anthracenyl group, a fluorenyl group, a carbazolyl group, and a pyrenyl group which are optionally substituted with a $C_1$-$C_5$ alkyl group, a $C_1$-$C_5$ alkoxy group, a cyano group, an amine group, a phenoxy group, a phenyl group or a halogen group; or a substituted $C_3$-$C_{60}$ heteroaryl group which is optionally substituted with a $C_1$-$C_5$ alkyl group, a $C_1$-$C_5$ alkoxy group, a cyano group, an amine group, a phenoxy group, a phenyl group, a halogen group, or a $C_3$-$C_{10}$ heteroaryl group.

$R_2$ and $R_3$ may be each independently a methyl group or a phenyl group.

The heterocyclic compound may include one of the compounds below:

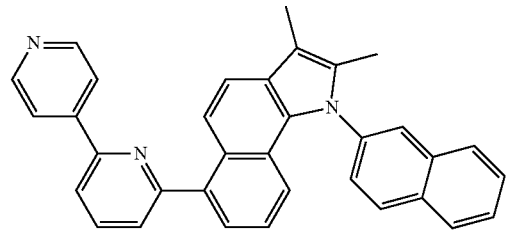

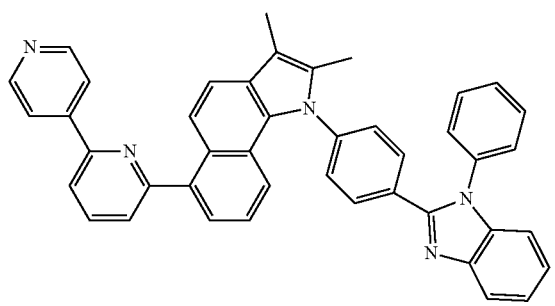

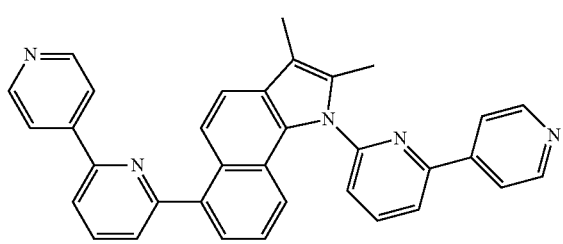

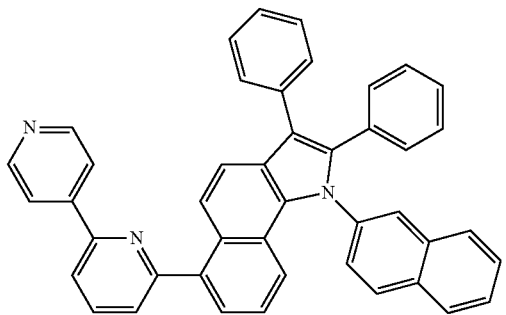

According to another aspect of the present embodiments, there is provided an organic light-emitting device including: a first electrode; a second electrode; and an organic layer between the first electrode and the second electrode, wherein the organic layer includes at least one layer including the above heterocyclic compound.

The organic layer may include an electron injection layer or an electron transport layer.

The organic layer may include a single layer having both an electron injection function and an electron transport function.

The organic layer may include an emission layer.

The organic layer may include an emission layer, and the heterocyclic compound may be used as a host for a fluorescent or phosphorescent device.

The organic layer may include an emission layer, and the heterocyclic compound may be used as a fluorescent dopant.

The emission layer, the electron injection layer, or the electron transport layer of the organic light-emitting device may include the heterocyclic compound, wherein the emission layer may include an anthracene compound, or a styryl compound.

The electron injection layer or the electron transport layer of the organic light-emitting device may include the heterocyclic compound, and a red emission layer, a green emission layer, a blue emission layer, or a white emission layer may include a phosphorescent compound.

The organic layer may include at least one layer selected from the group consisting of a hole injection layer, a hole transport layer, an electron blocking layer, an emission layer, a hole blocking layer, an electron transport layer, and an electron injection layer.

The organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport structure layer/electron injection layer/second electrode structure.

According to another aspect of the present embodiments, there is provided a flat panel display device including the above organic light-emitting device, wherein the first electrode of the organic light-emitting device is electrically connected to a source electrode or a drain electrode of a thin-film transistor.

According to another aspect of the present embodiments, there is provided an organic light-emitting device including: a first electrode; a second electrode; and an organic layer between the first electrode and the second electrode, wherein the organic layer includes at least one layer including the above heterocyclic compound, the at least one layer being formed using a wet process.

BRIEF DESCRIPTION OF THE DRAWINGS

The above and other features and advantages of the present embodiments will become more apparent by describing in detail example embodiments thereof with reference to the attached drawing in which:

FIG. 1 is a diagram of the structure of an organic light-emitting device according to an embodiment.

DETAILED DESCRIPTION

The present embodiments will now be described more fully with reference to the accompanying drawings, in which example embodiments are shown.

A heterocyclic compound according to an embodiment is represented by Formula 1 below:

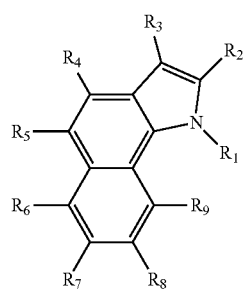

Formula 1 wherein $R_1$ through $R_9$ are each independently a hydrogen atom, a heavy hydrogen atom (deuterium or tritium), a substituted or unsubstituted $C_1$-$C_{50}$ alkyl group, a substituted or unsubstituted $C_3$-$C_{50}$ cycloalkyl group, a substituted or unsubstituted $C_1$-$C_{50}$ alkoxy group, a substituted or unsubstituted $C_5$-$C_{50}$ aryloxy group, a substituted or unsubstituted $C_5$-$C_{50}$ arylthio group, a substituted or unsubstituted $C_5$-$C_{60}$ aryl group, a substituted amino group with a $R_5$-$R_{60}$ aryl group, a substituted or unsubstituted $C_3$-$C_{60}$ heteroaryl group, a substituted or unsubstituted $C_6$-$C_{60}$ condensed polycyclic group, a halogen atom, a cyano group, a nitro group, a hydroxyl group, or a carboxyl group, wherein two vicinal substituents among $R_1$ through $R_9$ are linked to each other to form an aromatic ring.

Examples of materials for forming an emission layer or an electron transport layer, which constitute an organic light-emitting device, include, but are not limited to, Alq3, 2,2',2"-(1,3,5-phenylene)tris-(1-phenyl)-1H-benzimidazol (TPBI), 2-Biphenyl-4-yl-5-(4-tert-butyl-phenyl)-[1,3,4]oxadiazole (PBD), perfluorinated chemical (PF-6P), and 2,5-bis(6'-(2', 2"-bipyridyl))-1,1-dimethyl-3,4-diphenylsiylol (Py-PySPyPy).

An organic light-emitting device manufactured using the heterocyclic compound of Formula 1, in which a phenenthrene group and an indole group are fused, has excellent durability when stored or operated. In addition, due to the inclusion of a substituent such as a fluorene group or a naphthyl group, molecular layers formed as thin films may be maintained in good condition, thereby improving the characteristics of the organic light-emitting device.

Substituents in the heterocyclic compound of Formula 1 will now be described in detail.

In Formula 1 above, $R_1$, $R_2$, $R_3$ or $R_6$ may be an aryl group. The aryl group may be substituted with a substituent described later in conjunction with the $C_1$-$C_{50}$ alkyl group.

$R_6$ may be an unsubstituted monocyclic to tetracyclic aryl group selected from the group consisting of a phenyl group, a naphthyl group, a biphenyl group, a terphenyl group, an anthracenyl group, a fluorenyl group, a carbazolyl group, and a pyrenyl group; an unsubstituted $C_3$-$C_{60}$ heteroaryl group; an unsubstituted $C_5$-$C_{50}$ arylamine group; a substituted monocyclic to tetracyclic aryl group selected from the group consisting of a phenyl group, a naphthyl group, a biphenyl group, a terphenyl group, an anthracenyl group, a fluorenyl group, a carbazolyl group, and a pyrenyl group which are optionally substituted with a $C_1$-$C_5$ alkyl group, a $C_1$-$C_5$ alkoxy group, a cyano group, an amine group, a phenoxy group, a phenyl group, a halogen group or a $C_3$-$C_{10}$ heteroaryl group; a substituted $C_3$-$C_{60}$ heteroaryl group which is optionally substituted with a $C_1$-$C_5$ alkyl group, a $C_1$-$C_5$ alkoxy group, a cyano group, an amine group, a phenoxy group, a phenyl group or a halogen group; or a substituted $C_5$-$C_{50}$ arylamine group which is substututed with a $C_1$-$C_5$ alkyl group, a $C_1$-$C_5$ alkoxy group, a cyano group, an amine group, a phenoxy group, a phenyl group or a halogen group.

$R_1$ may be an unsubstituted monocyclic to tetracyclic aryl group selected from the group consisting of a phenyl group, a naphthyl group, a biphenyl group, a terphenyl group, an anthracenyl group, a fluorenyl group, a carbazolyl group, and a pyrenyl group; an unsubstituted $C_3$-$C_{60}$ heteroaryl group; a substituted monocyclic to tetracyclic aryl group selected from the group consisting of a phenyl group, a naphthyl group, a biphenyl group, a terphenyl group, an anthracenyl group, a fluorenyl group, a carbazolyl group, and a pyrenyl group which are optionally substituted with a $C_1$-$C_5$ alkyl group, a $C_1$-$C_5$ alkoxy group, a cyano group, an amine group, a phenoxy group, a phenyl group or a halogen group; or a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group, a halogen group, or a $C_3$-$C_{10}$ heteroaryl group.

$R_2$ and $R_3$ may be each independently a methyl group or a phenyl group.

Hereinafter, substituents described with reference to Formula 1 will now be described in detail. In this regard, the numbers of carbons in substituents are presented only for illustrative purposes and do not limit the characteristics of the substituents.

The unsubstituted $C_1$-$C_{50}$ alkyl group used herein may be linear or branched. Examples of the unsubstituted $C_1$-$C_{50}$ alkyl group include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with a heavy hydrogen atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_2$-$C_{10}$ alkenyl group, a $C_2$-$C_{10}$ alkynyl group, a $C_6$-$C_{16}$ aryl group, or a $C_3$-$C_{16}$ heteroaryl group.

The unsubstituted $C_3$-$C_{50}$ cycloalkyl group used herein refers to a $C_3$-$C_{50}$ cyclic alkyl group wherein at least one hydrogen atom in the cycloalkyl group may be substituted with a substituent such as those described above in connection with the $C_1$-$C_{50}$ alkyl group.

The unsubstituted $C_1$-$C_{50}$ alkoxy group used herein is a group having a structure of —OA wherein A is an unsubstituted $C_1$-$C_{50}$ alkyl group as described above. Examples of the unsubstituted $C_1$-$C_{50}$ alkoxy group include, but are not limited to, a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted $C_5$-$C_{60}$ aryl group used herein refers to a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with substituent such as those described above in conjunction with the $C_1$-$C_{50}$ alkyl group.

Examples of the substituted or unsubstituted $C_5$-$C_{60}$ aryl group include, but are not limited to, a phenyl group, a $C_1$-$C_{10}$ alkylphenyl group (for example, an ethylphenyl group), a halophenyl group (for example, o-, m-, and p-fluorophenyl group, a dichlorophenyl group), a cyanophenyl group, dicyanophenyl group, a trifluoromethoxyphenyl group, a biphenyl group, a halobiphenyl group, a cyanobiphenyl group, a $C_1$-$C_{10}$ alkyl biphenyl group, a $C_1$-$C_{10}$ alkoxybiphenyl group, an o-, m-, and p-tolyl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (for example, a fluoronaphthyl group), a $C_1$-$C_{10}$ alkylnaphthyl group (for example, a methylnaphthyl group), a $C_1$-$C_{10}$ alkoxynaphthyl group (for example, a methoxynaphthyl group), a cyanonaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted $C_3$-$C_{60}$ heteroaryl group used herein includes one, two or three hetero atoms selected from N, O, P and S. At least two rings may be fused to each other or linked to each other by a single bond. Examples of the unsubstituted $C_3$-$C_{60}$ heteroaryl group may include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, and an isoquinolinyl group. At least one hydrogen atom in the heteroaryl group may be substituted with a substituent such as those described above in conjunction with the $C_1$-$C_{50}$ alkyl group.

The unsubstituted $C_5$-$C_{50}$ aryloxy group is represented by —$OA_1$ wherein $A_1$ may be a $C_5$-$C_{50}$ aryl group. Examples of the aryloxy group may include a phenoxy group but are not limited to. At least one hydrogen atom in the aryloxy group may be substituted with a substituent such as those described above in conjunction with the $C_1$-$C_{50}$ alkyl group.

The unsubstituted $C_5$-$C_{50}$ arylthio group is represented by —$SA_1$ where $A_1$ may be a $C_5$-$C_{50}$ aryl group. Examples of the arylthio group include, but are not limited to, a benzenethio group, and a naphthylthio group. In the arylthio group, at least one hydrogen atom may be substituted with a substituent such as those described above in conjunction with the unsubstituted $C_1$-$C_{50}$ alkyl group.

The unsubstituted $C_6$-$C_{60}$ condensed polycyclic group used herein refers to a substituent including at least two rings wherein at least one aromatic ring and/or at least one non-aromatic ring are fused to each other.

The $C_5$-$C_{50}$ arylamine group refers to an amine group with a $C_5$-$C_{50}$ aryl group as a substituent.

Examples of the heterocyclic compound represented by Formula 1 may include Compounds 1 through 55 represented by the following formulae. However, the compounds represented by Formula 1 are not limited thereto.

1

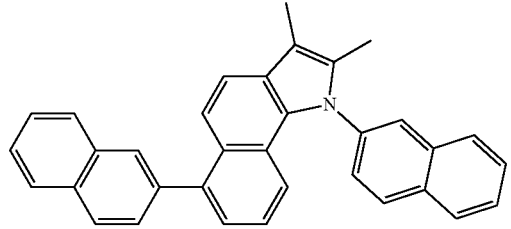

2

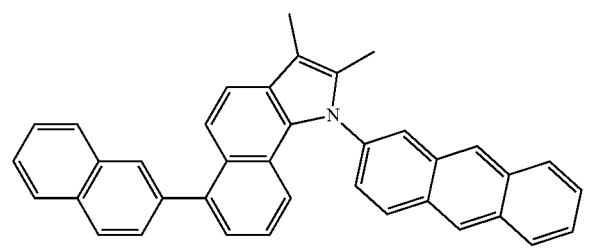

-continued

3

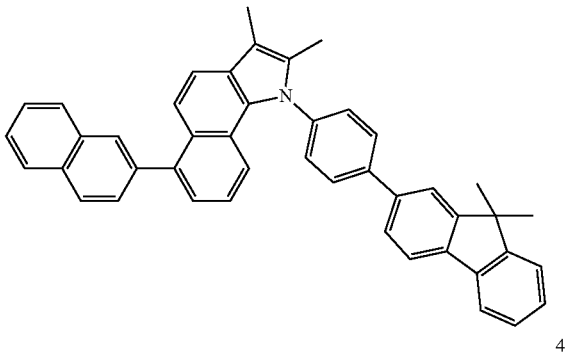

4

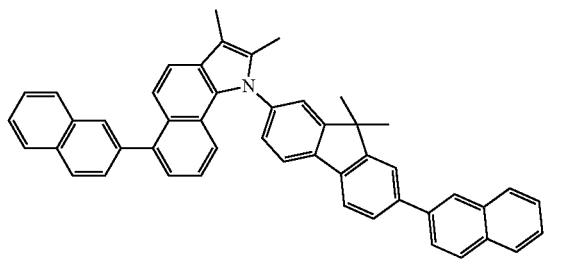

5

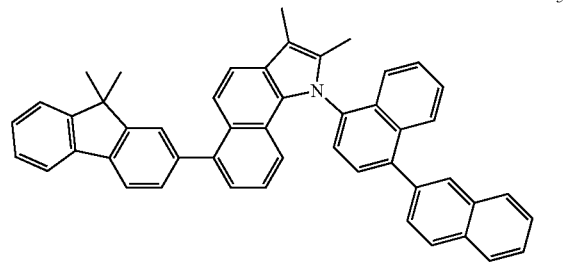

6

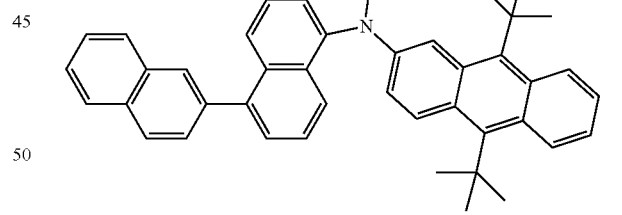

7

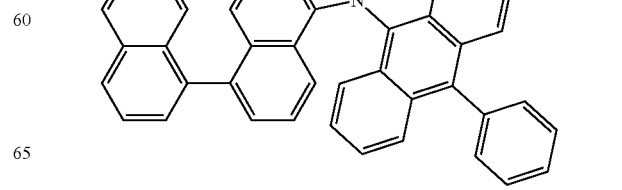

8
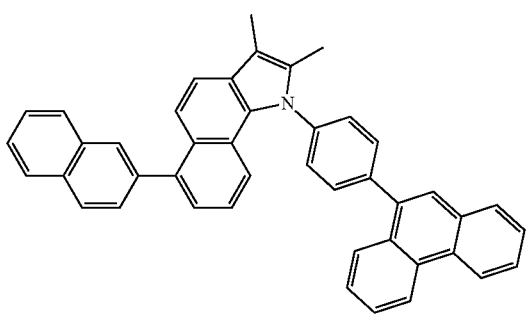
9
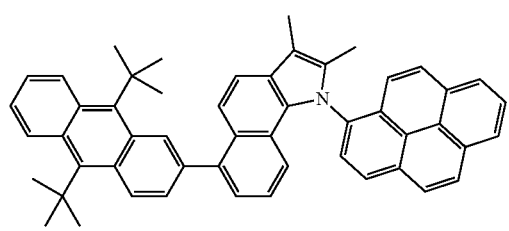
10
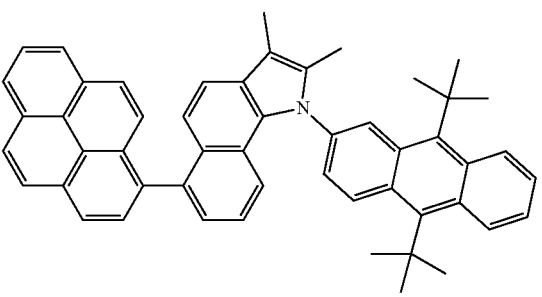
11
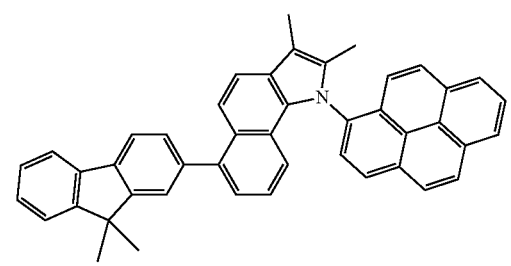
12
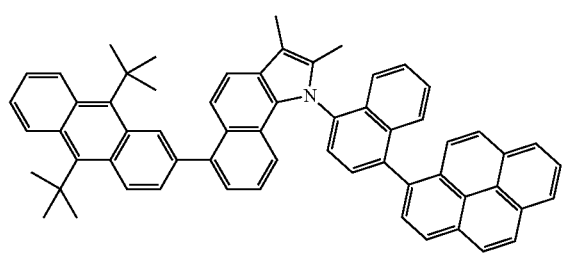
13
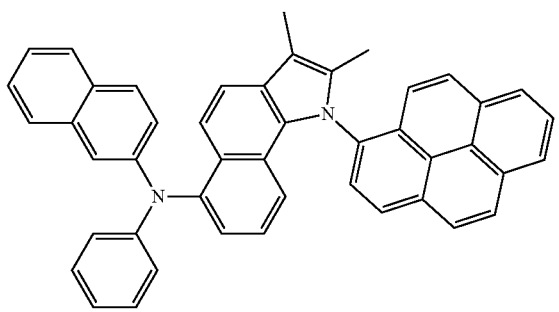
14
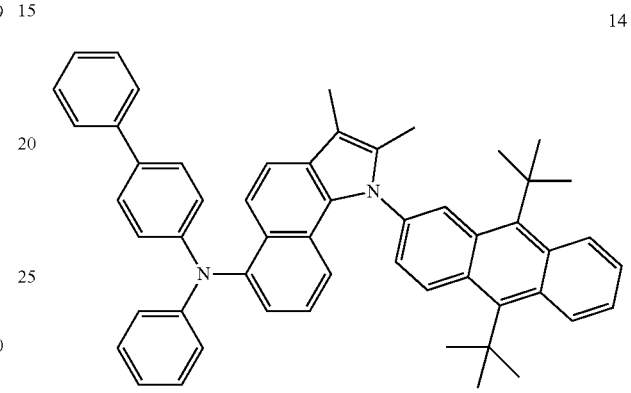
15
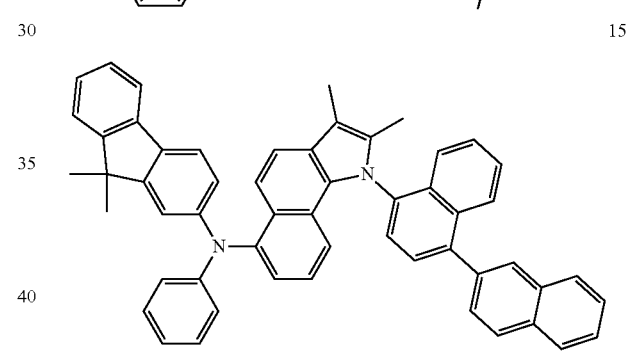
16
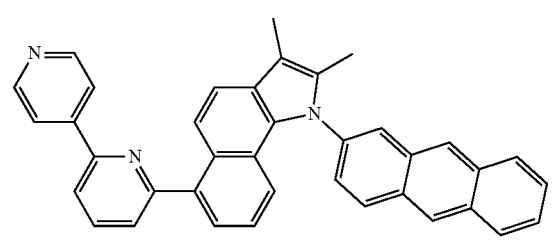
17
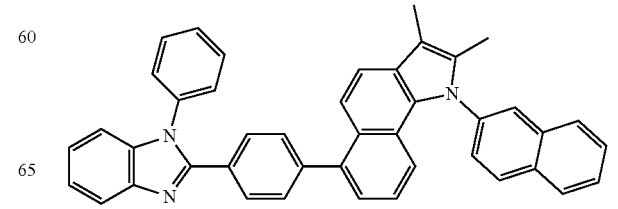

18
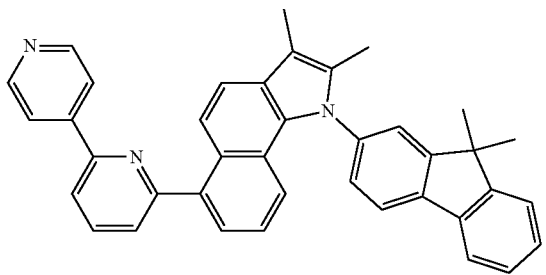
19
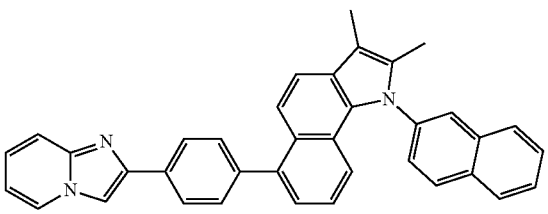
20
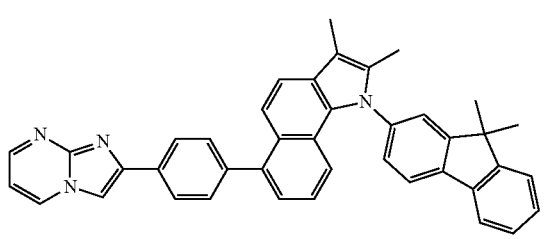
21
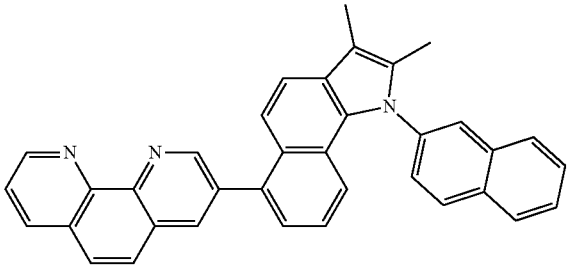
22
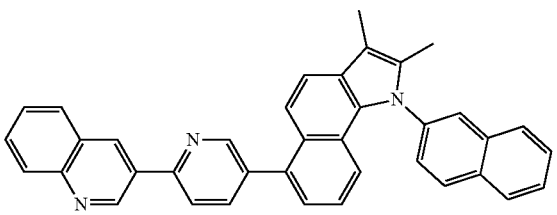
23
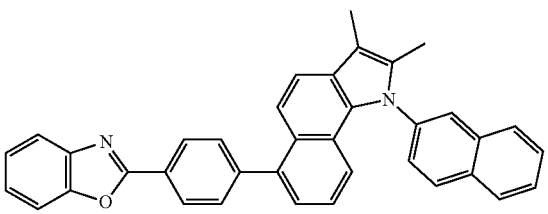
24
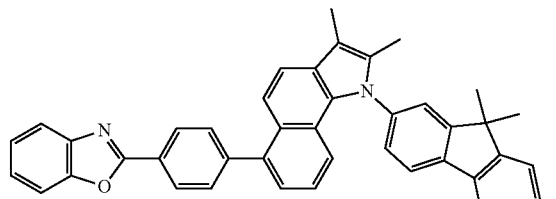
25
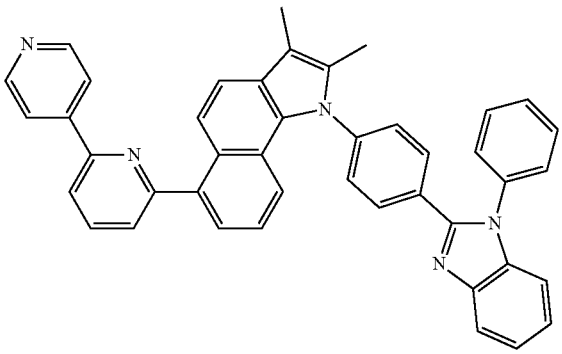
26
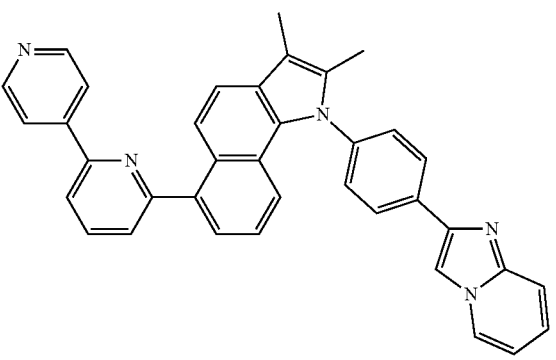
27
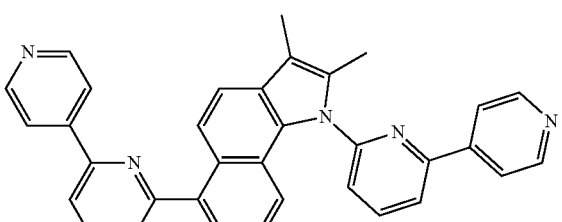
28
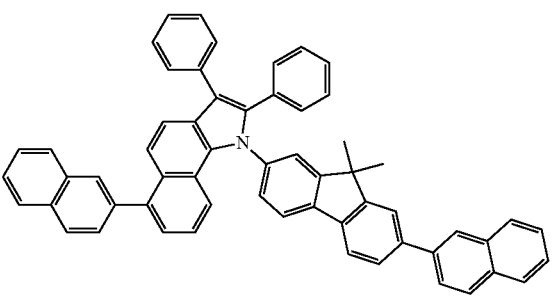

29
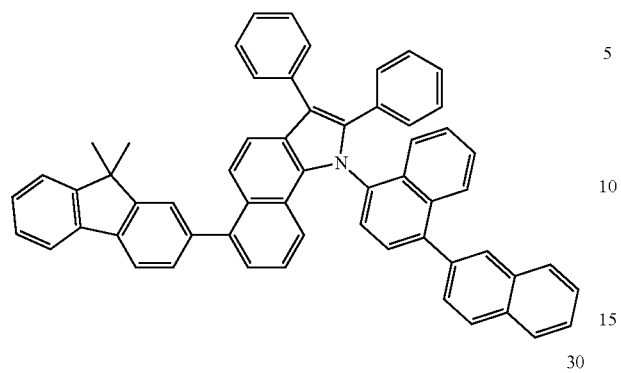
30
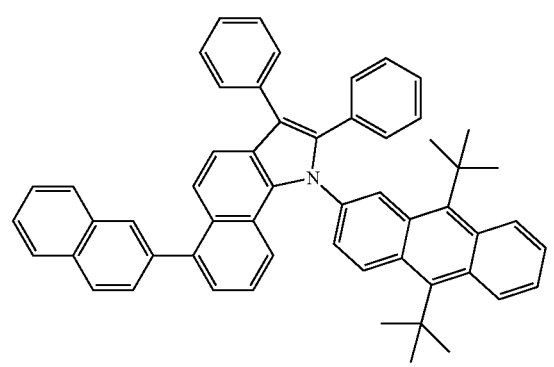
31
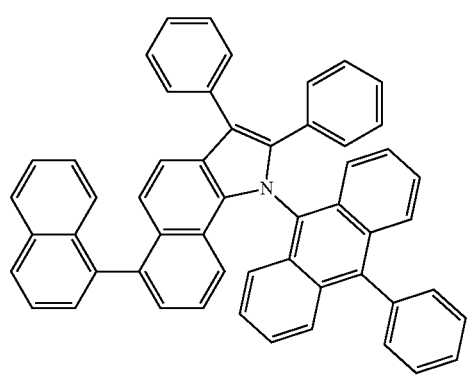
32
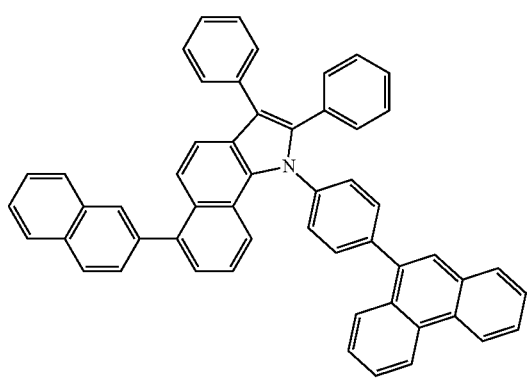
33
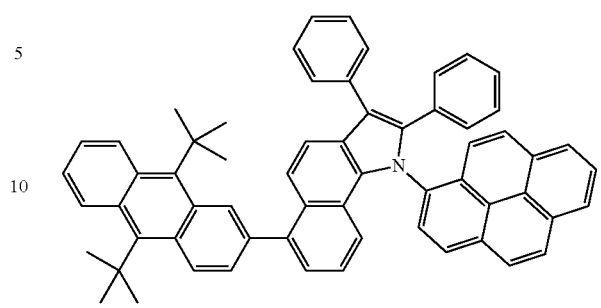
34
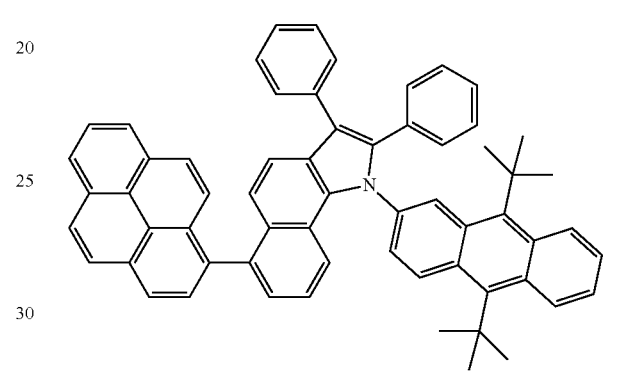
35
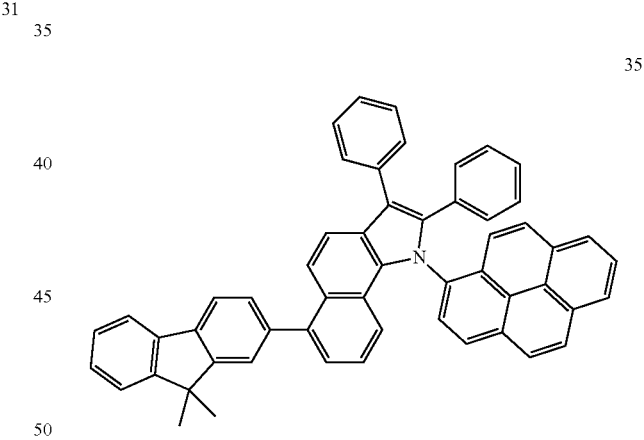
36
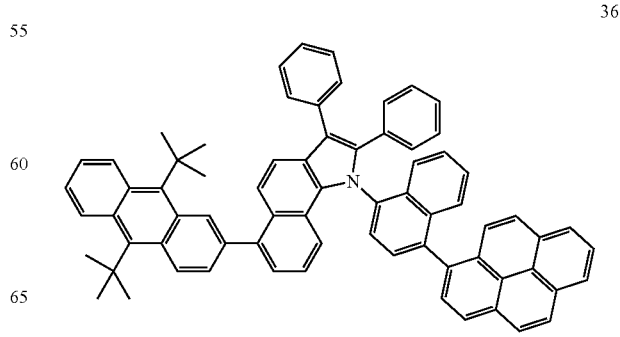

-continued
37
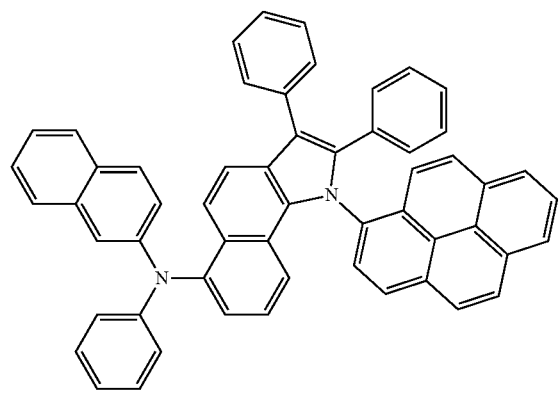
38
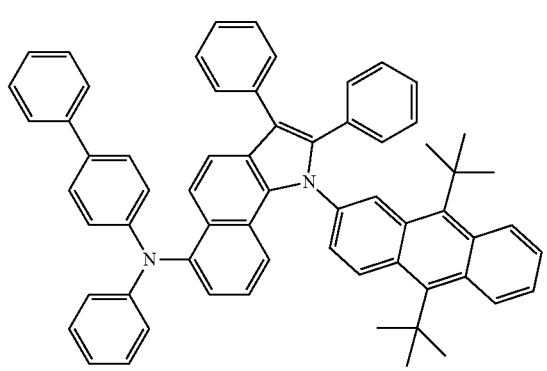
39
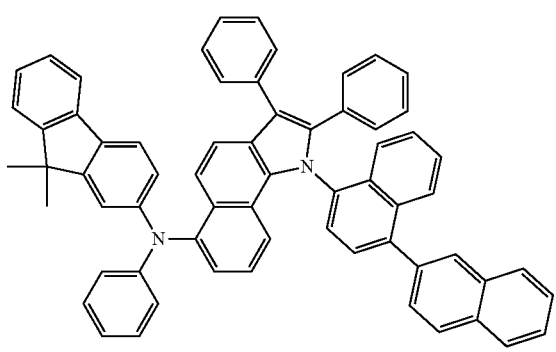
40
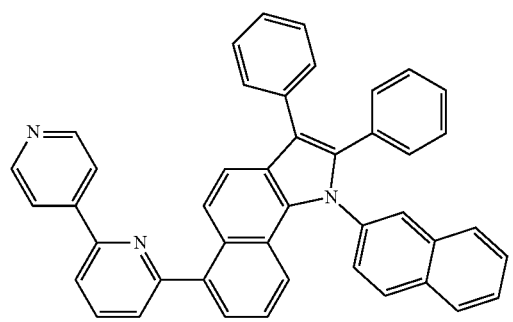
-continued
41
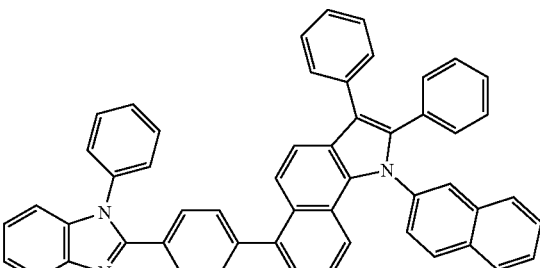
42
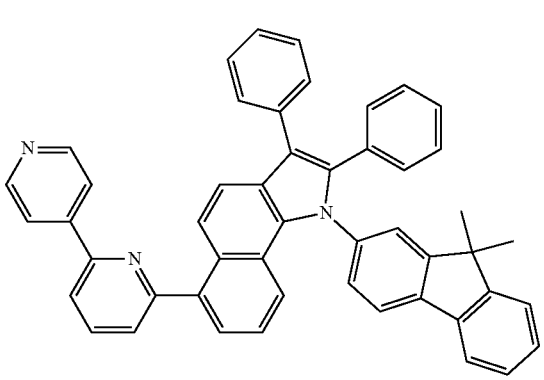
43
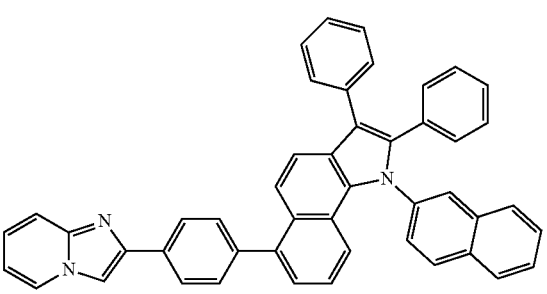
44

44
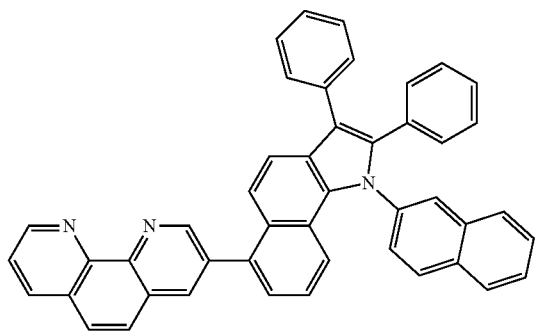
45
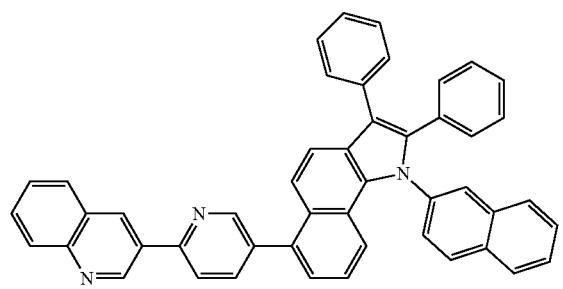
46
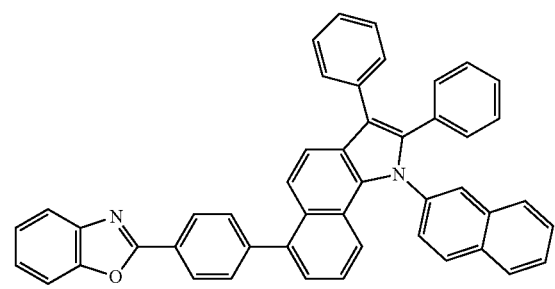
47
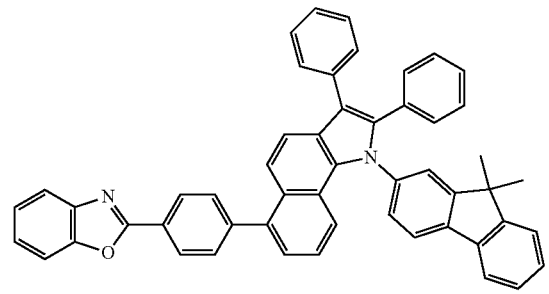
48
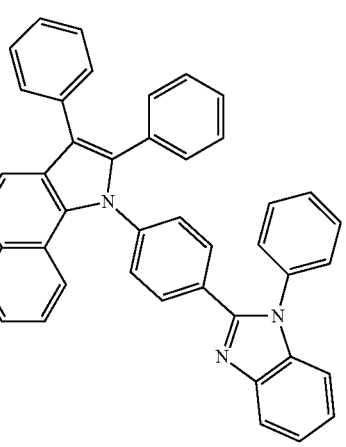
49
50
51
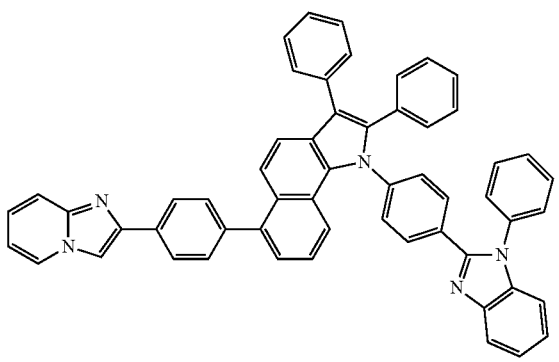

52

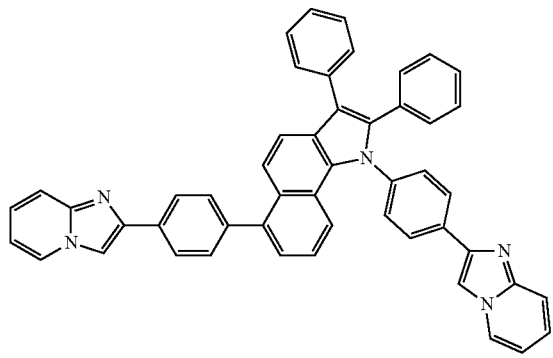

53

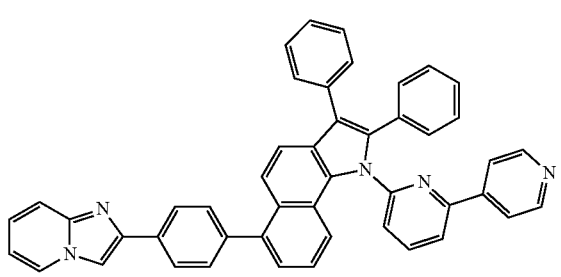

53

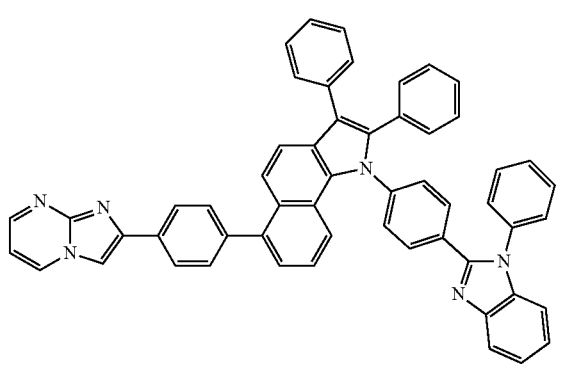

54

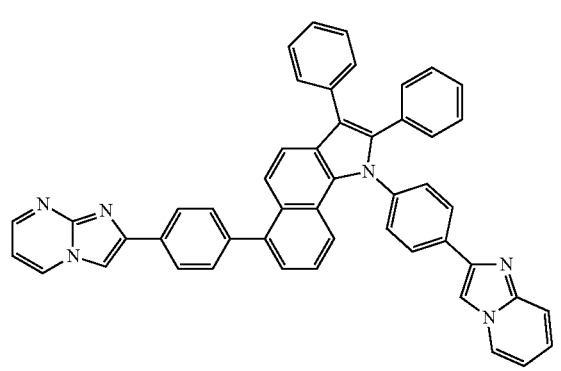

55

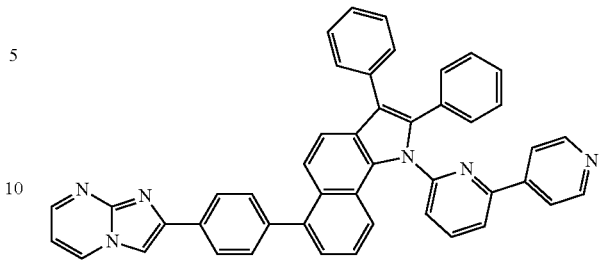

An organic light-emitting device according to an embodiment includes a first electrode, a second electrode, and an organic layer disposed between the first electrode and the second electrode, the organic layer including the heterocylic compound of Formula 1 described above.

The organic layer, which includes the heterocyclic compound of Formula 1, may be an electron injection layer, an electron transport layer, or a single layer having both the abilities to inject and transport electrons. Alternatively, the organic layer including the heterocyclic compound of Formula 1 may be an emission layer. When the organic layer including the heterocyclic compound of Formula 1 is an emission layer, the heterocyclic compound of Formula 1 may be used as a host for a fluorescent or phosphorescent device or a fluorescent dopant.

In the organic light-emitting device, when the emission layer, the electron injection layer or the electron transport layer includes the heterocyclic compound of Formula 1, the emission layer may include an anthracene compound, an arylamine compound or a styryl compound, wherein the anthracene compound, the arylamine compound or the styryl compound may be unsubstituted or substituted with a substituent described above in conjunction with the $C_1$-$C_{50}$ alkyl group.

In the organic light-emitting device, when the electron injection layer or the electron transport layer includes the heterocyclic compound of Formula 1, a red emission layer, a green emission layer, a blue emission layer or a white emission layer may include a phosphorescent compound.

In some embodiments, the organic layer of the organic light-emitting device may further include, but is not limited to, a hole injection layer, a hole transport layer, a functional layer having both hole injection and transport functions, an emission layer, a hole blocking layer, an electron transport layer, an electron injection layer, of a combination of at least two of these layers. At least one of the hole injection layer, the hole transport layer, and the functional layer having both hole injection and transport functions, may further include, in addition to the heterocylic compound of Formula 1 and widely-known hole injection and transport materials, a charge-generating material for improving conductivity of the layer.

The charge-generating material may include, for example, a p-dopant. Nonlimiting examples of the p-dopant include quinine derivatives, including tetracyanoquinondimethane (TCNQ) and 2,3,5,6-tetrafluoro-tetracyano-1,4-benzoquinonedimethane (F4TCNQ); metal oxides, including tungsten oxide and molybdenum oxide; and cyano group-containing compounds, including a compound represented by Formula 100 below.

Formula 100

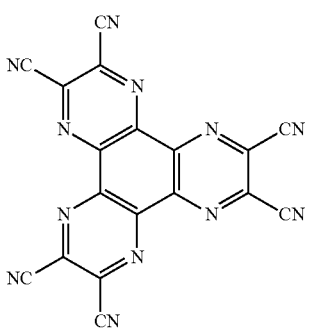

In some embodiments, when the hole injection layer, the hole transport layer, or the functional layer having both hole injection and transport functions further includes the charge-generating material, the charge-generating material may be uniformly or nonuniformly distributed in the layer.

In one embodiment, the electron transport layer of the organic light-emitting device may include an electron transporting organic compound and a metal-containing material. Nonlimiting examples of the electron transporting organic compound include ADN(9,10-di(naphthalene-2-yl)anthracene); and anthracene-based compounds, including a compound of Formula 101 and a compound of Formula 102 below.

Formula 101

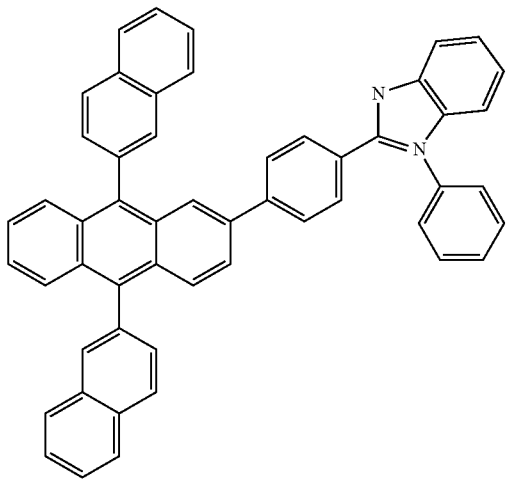

Formula 102

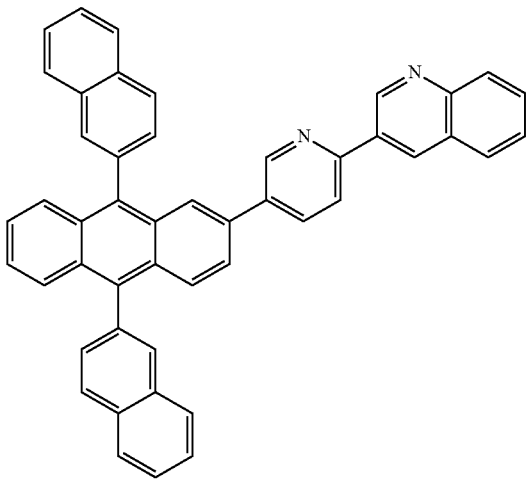

The metal-containing material may include a Li complex. Nonlimiting examples of the Li complex include lithium quinolate (LiQ) and a compound of Foimula 103 below.

Formula 103

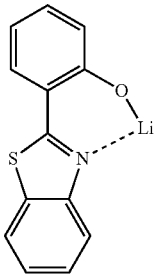

The first electrode may be an anode, and the second electrode may be a cathode, but the reverse is also possible.

In the organic light-emitting described above, the organic layer may further include at least one layer selected from the group consisting of a hole injection layer, a hole transport layer, an electron blocking layer, an emission layer, a hole blocking layer, an electron transport layer and an electron injection layer, if required.

For example, the organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode structure. Alternatively, the organic light-emitting device may have a first electrode/single layer having both hole injection and hole transport capabilities/emission layer/electron transport layer/second electrode structure, or a first electrode/single layer having both hole injection and hole transport capabilities/emission layer/electron transport layer/electron injection layer/second electrode structure.

According to some embodiments, the organic light-emitting device may be either a top-emission organic light-emitting device or a bottom-emission organic light-emitting device.

Hereinafter, a method of manufacturing an organic light-emitting device according to an embodiment will be described with reference to FIG. 1. FIG. 1 illustrates the structure of an organic light-emitting device according to an embodiment. Referring to FIG. 1, the organic light-emitting device according to the present embodiment includes a substrate (not shown), a first electrode (anode), a hole injection layer (HIL), a hole transport layer (HTL), an emission layer (EML), an electron transport layer (ETL), an electron injection layer (EIL), and a second electrode (cathode).

First, the first electrode is formed on the substrate by using a deposition or sputtering method. The first electrode may comprise a first electrode material having a high work function. The first electrode may constitute an anode or a cathode. The substrate may be a substrate conventionally used in organic light-emitting devices, and may include, for example, a glass substrate or a transparent plastic substrate with excellent mechanical strength, thermal stability, transparency, surface smoothness, ease of handling, and water resistance. Examples of the first electrode material include materials, such as indium tin oxide (ITO), indium zinc oxide (IZO), tin oxide ($SnO_2$), zinc oxide (ZnO), aluminum (Al), silver (Ag), and magnesium (Mg), which have excellent conductivity. The first electrode may be formed as a transparent or reflective electrode.

Next, the HIL may be formed on the first electrode using various methods, for example, vacuum deposition, spin coating, casting, Langmuir-Blodgett (LB) deposition, or the like.

When the HIL is formed using vacuum deposition, the deposition conditions may vary according to the material used to form the HIL, and the structure and thermal characteristics of the HIL. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, coating conditions may vary according to the material used to faun the HIL, and the structure and thermal properties of the HIL. For example, the coating conditions may include a coating rate of about 2000 rpm to about 5000 rpm, and a thermal treatment temperature of about 80° C. to about 200° C., wherein the thermal treatment serves to remove the solvent after coating.

The HIL may comprise any material that is commonly used to form a HIL. Examples of the material that can be used to form the HIL include a phthalocyanine compound such as copper phthalocyanine, 4,4',4"-tris(3-methylphenylphenylamino) triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS), but are not limited thereto.

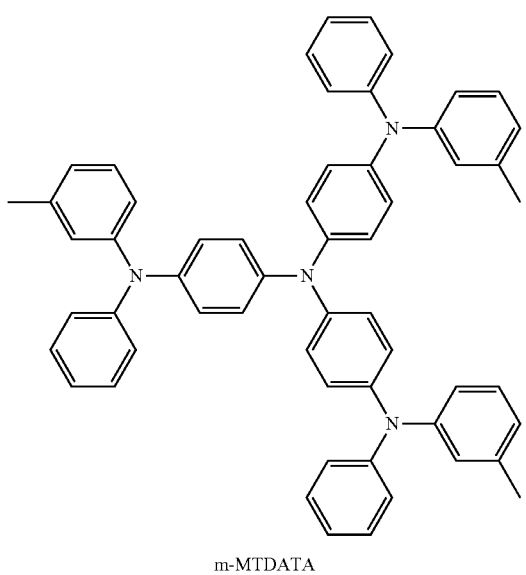

m-MTDATA

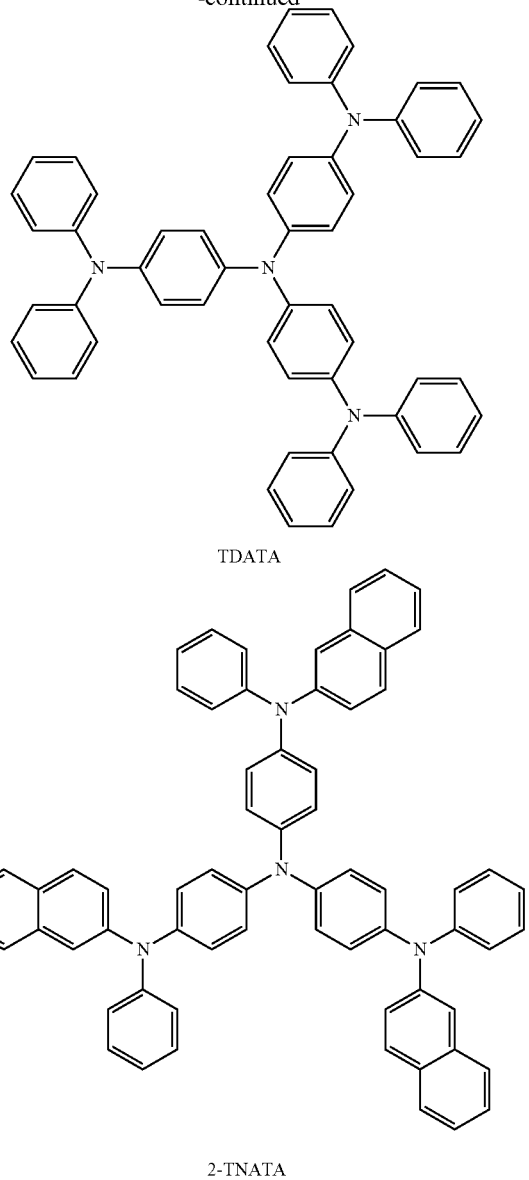

TDATA

2-TNATA

The HIL may have a thickness of about 100 Å to about 10000 Å. When the thickness of the HIL is within these ranges, the HIL may have good hole injection characteristics without an increase in driving voltage.

Next, the HTL may be formed on the HIL using various methods, for example, vacuum deposition, spin coating, casting, LB deposition, or the like. When the HTL is formed using vacuum deposition or spin coating, the deposition or coating conditions may be similar to those used to form the HIL, though the deposition or coating conditions may vary according to the material that is used to form the HTL.

Alternatively, known HTL materials may be used. Examples of such HTL materials include, but are not limited to, carbazole derivatives such as N-phenylcarbazole or polyvinylcarbazole, and amine derivatives having an aromatic condensed ring, such as NPB, N,N'-bis(3-methylphenyl)-N, N'-diphenyl-[1,1-biphenyl]-4,4'-diamine (TPD), or the like. For example, TCTA may not only transport holes but also inhibit excitons from being diffused from the EML.

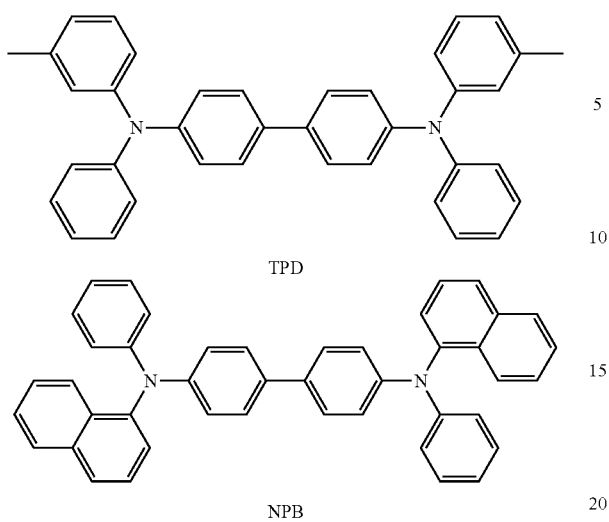

TPD

NPB

The HTL may have a thickness of about 50 Å to about 1000 Å, for example, a thickness of about 100 Å to about 600 Å. When the thickness of the HTL is within these ranges, the HTL may have good hole transport characteristics without a substantial increase in driving voltage.

Next, the EML may be formed on the HTL using various methods, for example, vacuum deposition, spin coating, casting, LB deposition, or the like. When the EML is formed using vacuum deposition or spin coating, the deposition or coating conditions may be similar to those used to form the HIL, though the deposition or coating conditions may vary according to the material that is used to form the EML.

The EML may include the heterocyclic compound of Formula 1 described above. For example, the heterocyclic compound of Formula 1 may be used as a host or a dopant. The EML may be formed using a variety of light-emitting materials, in addition to the heterocyclic compound of Formula 1. Alternatively, the EML may also be formed using a host and a dopant. Dopants that may be used to form the EML may include either a fluorescent dopant or a phosphorescent dopant.

Examples of the host may include, but are not limited to, Alq3, 4,4'-N,N'-dicarbazole-biphenyl (CPB), 9,10-di(naphthalen-2-yl)anthracene (ADN), and distyrylarylene (DSA).

Examples of red dopants include, but are not limited to, platinum(II) octaethylporphyrin (PtOEP), Ir(piq)$_3$, Btp$_2$Ir(acac), and DCJTB (4-(dicyanomethylene)-2-t-butyl-6(1,1,7,7-tetramethyljulolidyl-9-enyl)-4H-pyran).

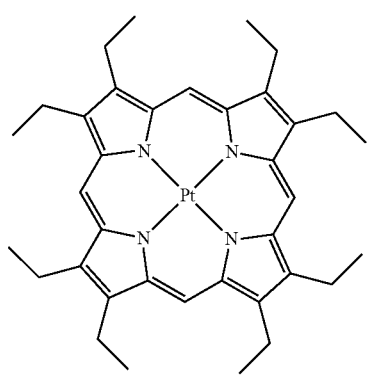

PtOEP

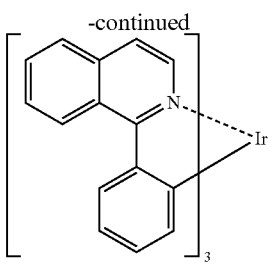

Ir(piq)$_3$

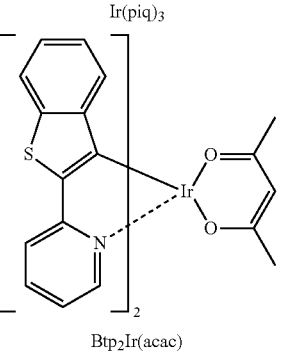

Btp$_2$Ir(acac)

Examples of green dopants include, but are not limited to, Ir(ppy)$_3$ (where "ppy" denotes phenylpyridine), Ir(ppy)$_2$(acac), Ir(mpyp)$_3$, and C545T.

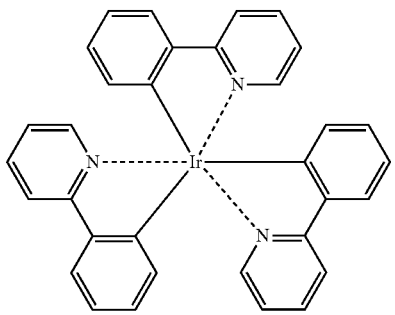

Ir(ppy)$_3$

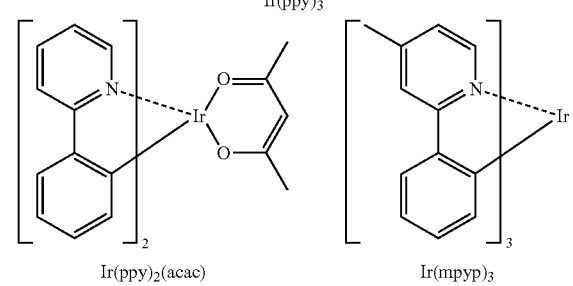

Ir(ppy)$_2$(acac)　　　　Ir(mpyp)$_3$

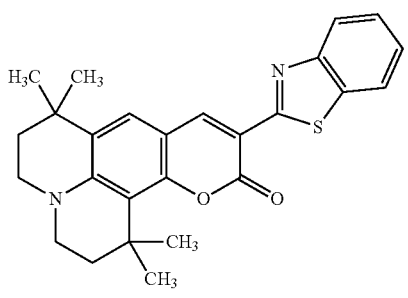

C545T

Examples of blue dopants include, but are not limited to, $F_2Irpic$, $(F_2ppy)_2Ir(tmd)$, $Ir(dfppz)_3$, ter-fluorene, 4,4'-bis(4-diphenylaminostyryl)biphenyl (DPAVBi), and 2,5,8,11-tetra-t-butyl pherylene (TBP).

The amount of the dopant may be in a range of about 0.1 to about 20 parts by weight, or about 0.5 to about 12 parts by weight, based on 100 parts by weight of the EML material (which is equivalent to the total weight of the host and the

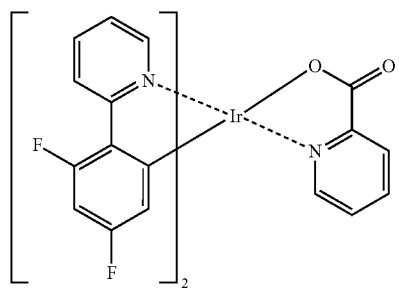

F₂Irpic

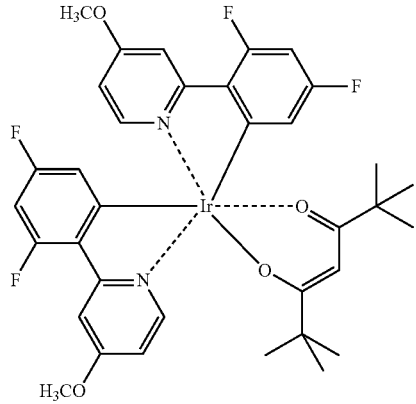

(F₂ppy)₂Ir(tmd)

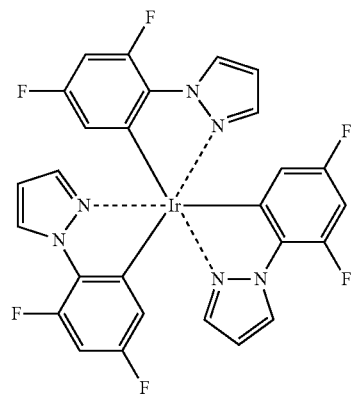

Ir(dfppz)₃

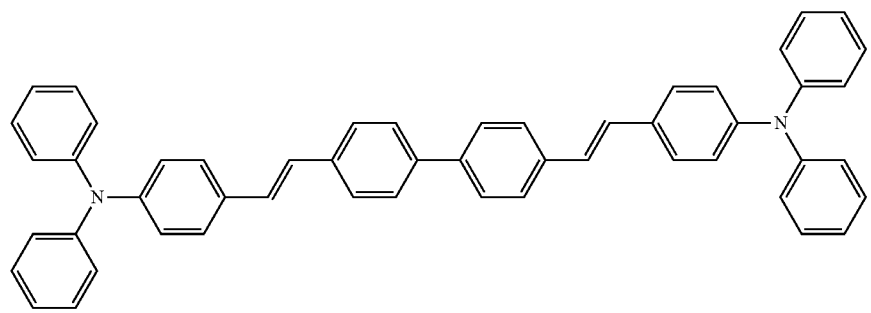

DPAVBi

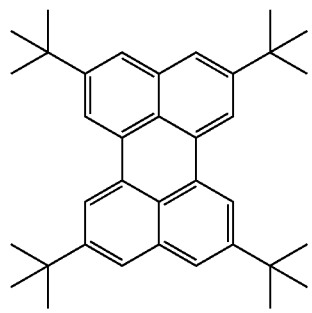

TBP dopant). When the amount of the dopant is within these ranges, concentration quenching may be substantially prevented.

The EML may have a thickness of about 100 Å to about 1,000 Å, for example, about 200 Å to about 600 Å. When the thickness of the EML is within these ranges, the EML may have good light-emitting characteristics without a substantial increase in driving voltage.

When the EML includes a phosphorescent dopant, a hole blocking layer (HBL, not shown in FIG. 1) may be formed on the EML in order to prevent diffusion of triplet excitons or holes into the ETL. In this case, the HBL may comprise any material commonly used to form a HBL, without limitation. Examples of such HBL materials include, but are not limited to, oxadiazole derivatives, triazole derivatives, phenathroline derivatives, BAlq, and BCP.

The HBL may have a thickness of about 50 Å to about 1,000 Å, for example, about 100 Å to about 300 Å. When the thickness of the HBL is within these ranges, the HBL may have good hole blocking characteristics without a substantial increase in driving voltage.

Next, the ETL is formed on the EML (or HBL) using various methods, for example, vacuum deposition, spin coating, casting, or the like. When the ETL is formed using vacuum deposition or spin coating, the deposition or coating conditions may be similar to those used to form the HIL, though the deposition or coating conditions may vary according to the material used to form the ETL.

The ETL material may include the heterocyclic compound of Formula 1 described above. Alternatively, the ETL may comprise any known material. Examples of the ETL material include, but are not limited to, quinoline derivatives, such as tris(8-quinolinolate)aluminum (Alq3), TAZ, and BAlq.

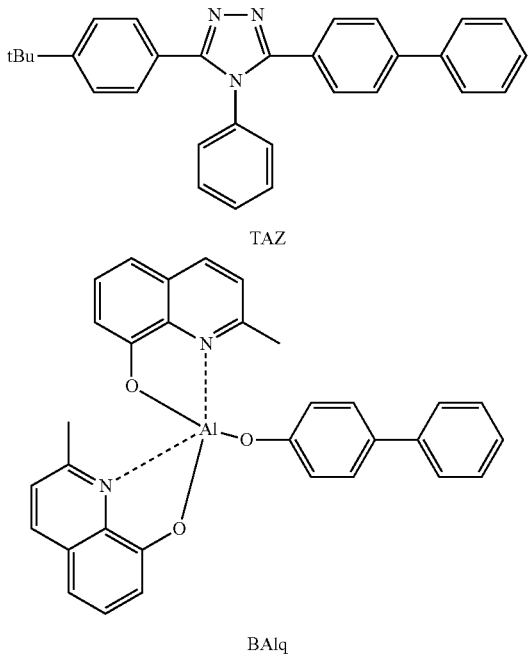

TAZ

BAlq

The ETL may have a thickness of about 100 Å to about 1,000 Å, for example, about 100 Å to about 500 Å. When the thickness of the ETL is within these ranges, the ETL may have good electron transport characteristics without a substantial increase in driving voltage.

In addition, the EIL, which facilitates injection of electrons from the cathode, may be formed on the ETL.

The EIL may include the heterocyclic compound of Formula 1 described above. Alternatively, EIL materials, such as LiF, NaCl, CsF, $Li_2O$, or BaO, may be used to form the EIL. The deposition or coating conditions for forming the EIL may be similar to those applied to form the HIL, though the deposition and coating conditions may vary according to the material that is used to form the EIL.

The EIL may have a thickness of about 1 Å to 100 Å, for example, about 5 Å to about 90 Å. When the thickness of the EIL is within these ranges, the EIL may have good electron injection characteristics without a substantial increase in driving voltage.

Finally, the second electrode may be formed on the EIL by using, for example, vacuum deposition, sputtering, or the like. The second electrode may be a cathode or an anode. The material for forming the second electrode may include a metal, an alloy, or an electrically conductive compound, which are materials having a low work function, or a mixture thereof Examples of such materials include, but are not limited to, lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission organic light-emitting device, a transparent cathode formed of a transparent material such as ITO or IZO may be used as the second electrode.

The organic light-emitting device according to some embodiments may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

At least one layer of the organic light-emitting device according to the embodiment described above may comprise the heterocyclic compound of Formula 1 by using a deposition method or a wet method of coating a solution of the heterocylic compound of Formula 1.

Hereinafter, synthesis examples of Compounds 16, 25, 27, and 40 and examples will be described in detail. However, these examples are for illustrative purposes only, and are not intended to limit the scope of the present embodiments.

Synthesis Examples

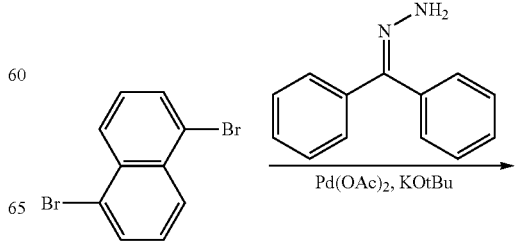

-continued

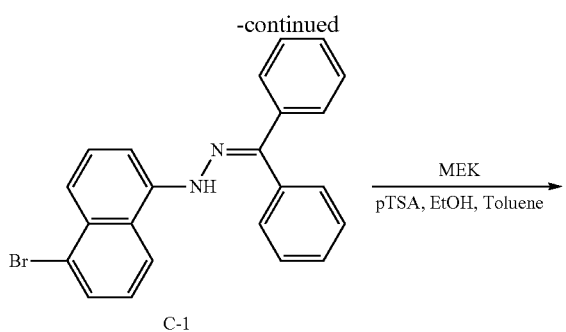

C-1

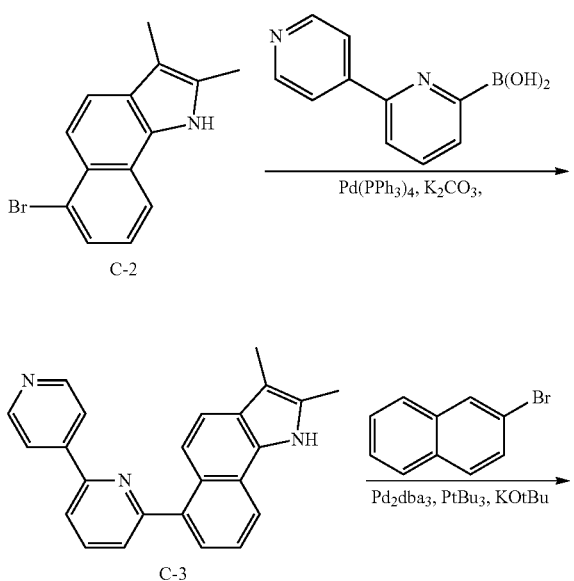

C-2

C-3

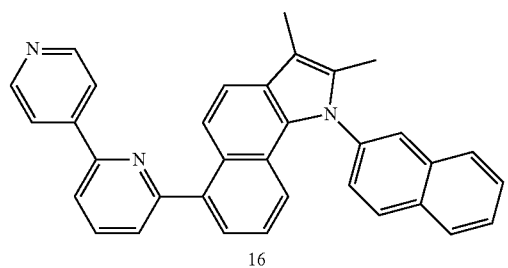

16

Synthesis of Intermediate C-1

300 mL of toluene was added to a mixture of 28.6 g (100 mmole) of 1,5-dibromonaphthalene, 11.7 g (60 mmole) of benzophenone hydrazone, 330 mg (3 mol %) of Pd(OAc)$_2$, and 7.3 g (75.0 mmole) of KOt-Bu and then heated at 90° C. in a nitrogen atmosphere for 4 hours. The reaction mixture was cooled to room temperature, and 100 mL of water was further added to the reaction mixture and was extracted twice with 500 mL of methylene chloride. The organic phase was dried, filtered, concentrated, and then separated using column chromatography to obtain 16.8 g of Compound C-1 in yellow solid form with a yield of 84%. The structure of Compound C-1 was identified using high-resolution mass spectrometry (HR-MS). (calc.; 400.0575, found; 400.0561)

Synthesis of Intermediate C-2

100 mL of toluene and 50 mL of ethanol were added to a mixture of 20.1 g (50 mmole) of Compound C-1, 38.0 g (200 mmole) of pTSA.H$_2$O and 50 mL of methyl ethyl ketone and then heated at 90° C. for 36 hours. The reaction mixture was cooled to room temperature, and 100 mL of water was further added to the reaction mixture and was extracted twice with 200 mL of methylene chloride. The organic phase was dried, filtered, concentrated, and then separated by column chromatography to obtain 9.3 g of Compound C-2 in light-green solid form with a yield of 68%. The structure of Compound C-2 was identified using high-resolution mass spectrometry (HR-MS). (calc.; 273.0153, found; 273.0148)

Synthesis of Intermediate C-3

30 mL of water and 100 mL of tetrahydrofuran (THF) were added to a mixture of 8.3 g (30 mmole) of Compound C-2, 6.6 g (33 mmole) of bipyridyl boronic acid, 1.7 g (5 mol %) of Pd(PPh$_3$)$_4$, and 4.8 g (120 mmole) of NaOH and then heated at 70° C. in a nitrogen atmosphere for 12 hours. The reaction mixture was cooled to room temperature, and 50 mL of water was further added to the reaction mixture and was extracted twice with 300 mL of methylene chloride. The organic phase was dried, filtered, concentrated, and then separated using column chromatography to obtain 6.07 g of Compound C-3 in pale-yellow solid form with a yield of 58%. The structure of Compound C-3 was identified using high-resolution mass spectrometry (HR-MS). (calc.; 349.1579, found; 349.1568)

Synthesis of Compound 16

100 mL of toluene was added to a mixture of 13.3 g (30.0 mmole) of Compound C-3, 8.07 g (39.0 mmole) of a 2-bromonaphthalene, 4.3 g (45.0 mmole) of NaOtBu, 1.4 g (1.5 mmole) of Pd$_2$(dba)$_3$, and 0.30 g (1.5 mmole) of PtBu$_3$ and then heated at 90° C. in a nitrogen atmosphere for 6 hours. The reaction mixture was cooled to room temperature, and 30 mL of water was further added to the reaction mixture and was extracted twice with 200 mL of methylene chloride. The organic phase was dried, filtered, concentrated, and then separated using column chromatography to obtain 9.2 g of Compound 16 in light-yellow solid form with a yield of 65%. The structure of Compound 16 was identified using nuclear magnetic resonance (NMR) spectroscopy and HR-MS.

1H-NMR (CDCl3, 400 MHz) δ (ppm); 8.12-8.75 (m, 5H), 6.89-7.78 (m, 19H), 2.44 (s, 3H), 2.41 (s, 3H). 13-C NMR (CDCl3, 100 MHz) δ (ppm); 162.2, 160.4, 158.6, 138.8, 138.4, 138.1, 136.7, 134.8, 133.8, 133.0, 132.2, 132.0, 130.7, 129.6, 129.0, 128,2, 127.2, 126.5, 126.2, 124.3, 122.6, 122.0 119.6, 119.2, 118.5, 118.0, 116.7, 116.4, 116.0, 114.2, 112,1, 12.1, 8.1.

HRMS (calc.; 475.2048, found; 475.2040)

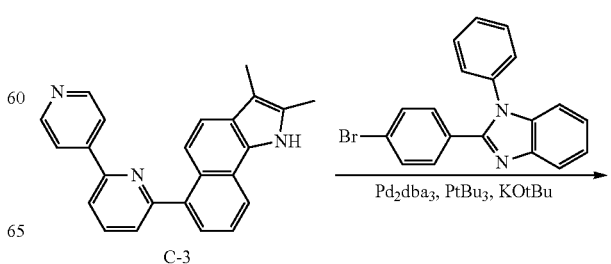

C-3

146.4, 139.8, 138.7, 137.8, 137.1, 136.5, 136.0, 134.3, 131.6, 131.0, 130.3, 129.1, 128.1, 127.4, 126.6, 126.1, 125.4, 124.8, 122.1, 119.8, 119.2, 118.5, 116.7, 116.4, 116.0, 114.2, 14.1, 9.5.
HRMS (calc.; 503.2110, found; 503.2101)

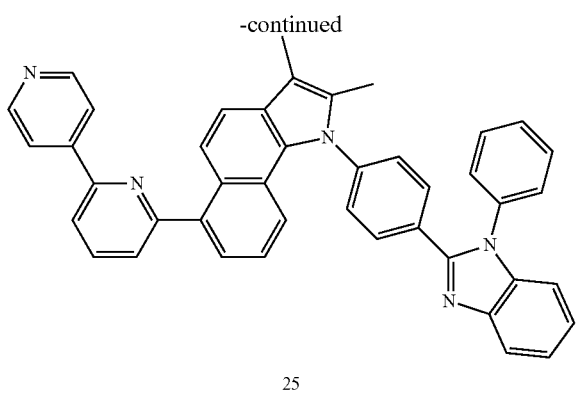

25

Synthesis of Compound 25

10.0 g of Compound 25 in light-yellow solid was synthesized with a yield of 50% by using 13.3 g (30 mmole) of Compound C-3 and 13.6 g (39 mmole) of 2-(4-bromo-phenyl)-1-phenyl-1H-benzoimidazole in the same manner as used in the synthesis of Compound 16. The structure of Compound 25 was identified using nuclear magnetic resonance (NMR) spectroscopy and HR-MS.

1H-NMR (CDCl3, 400 MHz) δ (ppm); 8.22-8.65 (m, 5H), 6.99-7.65 (m, 20H), 2.40 (s, 3H), 2.31 (s, 3H). 13-C NMR (CDCl3, 100 MHz) δ (ppm); 164.3, 162.3, 159.7, 140.8, 140.4, 139.4, 136.7, 135.8, 134.8, 133.7, 132.6, 132.0, 130.3, 129.1, 128.1, 127.2, 126.6, 126.1, 124.8, 122.1, 119.8, 119.2, 118.5, 118.0, 116.7, 116.4, 116.0, 114.2, 112,1, 15.1, 10.6.
HRMS (calc.; 617.2579, found; 617.2571)

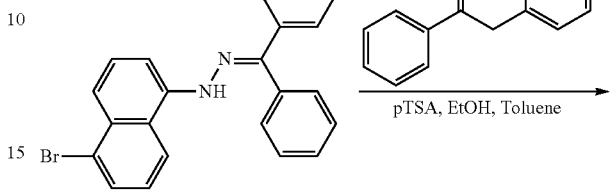

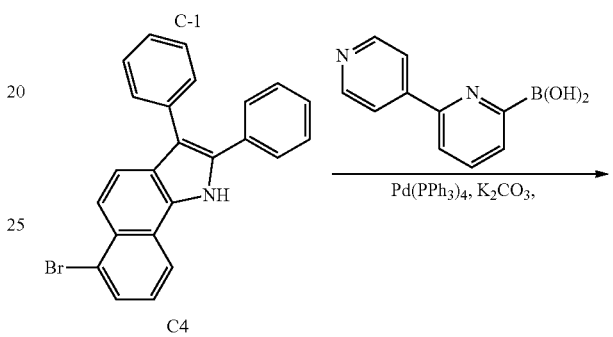

27

Synthesis of Compound 27

7.9 g of Compound 27 in light-yellow solid was synthesized with a yield of 43% by using 13.3 g (30 mmole) of Compound C-3 and 9.12 g (39 mmole) of 6-bromo bipyridyl in the same manner as used in the synthesis of Compound 16. The structure of Compound 27 was identified using nuclear magnetic resonance (NMR) spectroscopy and HR-MS.

1H-NMR (CDCl3, 400 MHz) δ (ppm); 8.02-8.43 (m, 4H), 7.02-7.85 (m, 15H), 2.42 (s, 3H), 2.32 (s, 3H). 13-C NMR (CDCl3, 100 MHz) δ (ppm); 160.3, 159.3, 158.3, 150.8,

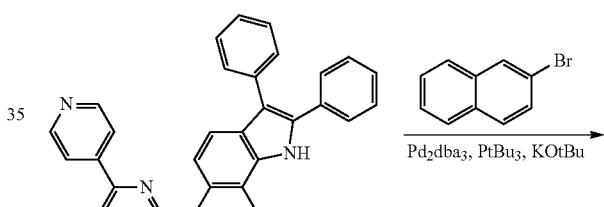

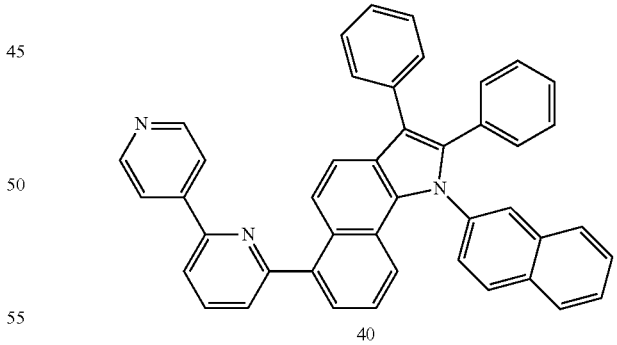

40

Synthesis of Intermediate C-4

12.3 g of Compound C-4 in pale-yellow solid form was synthesized with a yield of 62% in the same manner as used in the synthesis of Compound C-2, except that 19.6 g (100 mmole) of benzyl phenyl ketone was used, instead of methyethylketone. The structure of Compound C-4 was identified using high-resolution mass spectrometry (HR-MS). (calc.; 397.0466, found; 397.0456)

Synthesis of Intermediate C-5

10.6 g of Compound C-5 in pale-yellow solid was synthesized with a yield of 75% by using 11.9 g (30 mmole) of Compound C-4 and 6.6 g (33 mmole) of bipyridyl boronic acid in the same manner as used in the synthesis of Compound C-3. The structure of Compound C-5 was identified using high-resolution mass spectrometry (HR-MS). (calc.; 473.1892, found; 473.1883)

Synthesis of Compound 40

8.8 g of Compound 40 in light-yellow solid was synthesized with a yield of 62% by using 13.0 g (30 mmole) of Compound C-5 and 6.8 g (39 mmole) of bromonaphthalene in the same manner as used in the synthesis of Compound 16. The structure of Compound 40 was identified using nuclear magnetic resonance (NMR) spectroscopy and HR-MS.

$^1$H-NMR (CDCl$_3$, 400 MHz) δ (ppm); 8.23-8.53 (m, 5H), 7.06-7.86 (m, 24H). 13-C NMR (CDCl3, 100 MHz) δ (ppm); 158.3, 153.3, 152.3, 139.7, 138.5, 137.5, 137.1, 136.5, 136.2, 135.3, 134.2, 133.5, 132.1, 131.6, 131.0, 130.3, 129.1, 128.1, 127.8, 127.4, 126.6, 126.1, 125.4, 124.8, 122.1, 121.7, 121.0, 119.8, 119.2, 118.5, 116.7, 116.4, 116.0, 114.2.

HRMS (calc.; 599.2361, found; 599.2352)

Example 1

An anode was prepared by cutting a Corning 15 Ωcm$^2$ (1200 Å) ITO glass substrate to a size of 50 mm×50 mm×0.7 mm, ultrasonically cleaning the glass substrate using isopropyl alcohol and pure water for 5 minutes each, and then irradiating UV light for 30 minutes and exposing to ozone to clean. Then, the anode was mounted in a vacuum deposition apparatus.

Then, 2-TNATA (which is an HIL material) was vacuum-deposited on the glass substrate to form a HIL having a thickness of about 600 Å. Then, 4,4'-bis[N-(1-naphthyl)-N-phenylamino]biphenyl (NPB) (which is a hole transporting compound) was vacuum-deposited on the HIL to form a HTL having a thickness of about 300 Å.

Then, a green fluorescent host (Alq3) and a green fluorescent dopant (C545T) were simultaneously deposited in a weight ratio of 98:2 on the HTL, to form an EML having a thickness of about 300 Å.

Then, Compound 16 was deposited on the EML to form an ETL having a thickness of about 300 Å, and then LiF (which is halogenated alkali metal) was deposited on the ETL to form an EIL having a thickness of about 10 Å. Then, Al was vacuum-deposited on the EIL to a thickness of about 3000 Å to form a LiF/Al electrode (cathode), thereby completing the manufacture of an organic light-emitting device.

The organic light-emitting device had a driving voltage of 5.97 V at a current density of 50 mA/cm$^2$, a high luminosity of 8,454 cd/m$^2$, color coordinates of (0.311, 0.642), and a luminescent efficiency of 16.91 cd/A.

Example 2

An organic light-emitting device was manufactured in the same manner as in Example 1, except that Compound 25 was used instead of Compound 16 to form the ETL.

The organic light-emitting device had a driving voltage of 5.63 V at a current density of 50 mA/cm$^2$, a high luminosity of 8,848 cd/m$^2$, color coordinates of (0.310, 0.642), and a luminescent efficiency of 17.70 cd/A.

Example 3

An organic light-emitting device was manufactured in the same manner as in Example 1, except that Compound 27 was used instead of Compound 16 to form the ETL.

The organic light-emitting device had a driving voltage of 5.82 V at a current density of 50 mA/cm$^2$, a high luminosity of 8,376 cd/m$^2$, color coordinates of (0.309, 0.643), and a luminescent efficiency of 16.75 cd/A.

Example 4

An organic light-emitting device was manufactured in the same manner as in Example 1, except that Compound 40 was used instead of Compound 16 to form the ETL.

The organic light-emitting device had a driving voltage of 5.58 V at a current density of 50 mA/cm$^2$, a high luminosity of 8,651 cd/m$^2$, color coordinates of (0.310, 0.642), and a luminescent efficiency of 17.30 cd/A.

Comparative Example 1

An organic light-emitting device was manufactured in the same manner as in Example 1, except that Alq3 was used, instead of Compound 16, to form the ETL.

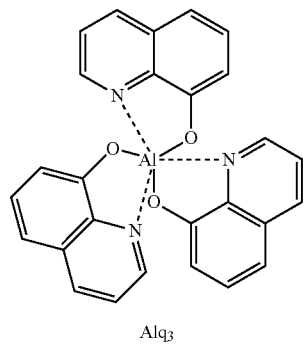

Alq3

The organic light-emitting device had a driving voltage of 7.45 V at a current density of 50 mA/cm$^2$, a luminosity of 6,102 cd/m$^2$, color coordinates of (0.309, 0.642), which are almost the same as those of Examples 1 through 4, and a luminescent efficiency of 12.2 cd/A.

The organic light-emitting devices including the ETL manufactured using the heterocyclic compounds of Formula 1 according to the present embodiments had a driving voltage that was lower by 1V or greater than devices manufactured using Alq3, and thus had higher efficiency and good I-V-L characteristics. In particular, lifetime characteristics were markedly improved by 100% or greater in the organic light-emitting devices of Examples 1 through 4, as compared to the organic light-emitting device of Comparative Example 1.

TABLE 1

|  | Electron Transport Material | Driving Voltage (V) | Current Density (mA/cm$^2$) | Luminance (cd/m$^2$) | Luminescent Efficiency (cd/A) | Color Coordinates | Half Lifespan (hr @100 mA/cm$^2$) |
|---|---|---|---|---|---|---|---|
| Example 1 | Compound 16 | 5.97 | 50 | 8,454 | 16.91 | (0.311, 0.642) | 495 hr |
| Example 2 | Compound 25 | 5.63 | 50 | 8,848 | 17.70 | (0.310, 0.642) | 550 hr |
| Example 3 | Compound 27 | 5.82 | 50 | 8,376 | 16.75 | (0.309, 0.643) | 480 hr |
| Example 4 | Compound 40 | 5.58 | 50 | 8,651 | 17.30 | (0.310, 0.642) | 523 hr |
| Comparative Example 1 | Alq3 | 7.45 | 50 | 6,102 | 12.2 | (0.309, 0.642) | 237 hr |

As described above, novel heterocyclic compounds according to the one or more of the above embodiments have good electrical characteristics, good charge transporting capabilities and good emission characteristics, and may be used to prevent crystallization due to high glass transition temperatures ($T_g$). The heterocyclic compounds may also be used as electron transporting materials for most color-fluorescent and phosphorescent devices, such as red, green, blue, and white fluorescent and phosphorescent devices, or as red, green, blue or white-light emitting materials. Thus, an organic light-emitting device with high-efficiency, low-driving voltage, high luminance and long lifespan may be manufactured using the heterocyclic compounds.

While the present embodiments have been particularly shown and described with reference to example embodiments thereof, it will be understood by those of ordinary skill in the art that various changes in form and details may be made therein without departing from the spirit and scope of the present embodiments as defined by the following claims.

What is claimed is:

1. A heterocyclic compound represented by Formula 1 below:

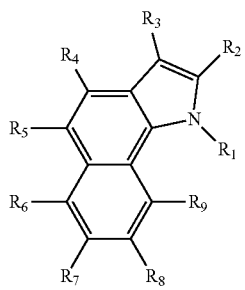

wherein $R_1$ is an unsubstituted monocyclic to tetracyclic aryl group selected from the group consisting of a naphthyl group, a biphenyl group, a terphenyl group, an anthracenyl group, a fluorenyl group, and a pyrenyl group; an unsubstituted $C_3$-$C_{60}$ heteroaryl group; a substituted monocyclic to tetracyclic aryl group selected from the group consisting of a naphthyl group, a biphenyl group, a terphenyl group, an anthracenyl group, a fluorenyl group, and a pyrenyl group which is substituted with a $C_1$-$C_5$ alkyl group, a $C_1$-$C_5$ alkoxy group, a cyano group, an amine group, a phenoxy group, a phenyl group or a halogen group; and a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group, a halogen group, or a $C_3$-$C_{10}$ heteroaryl group;

$R_2$ and $R_3$ are each independently a methyl group or a phenyl group;

$R_6$ is an unsubstituted monocyclic to tetracyclic aryl group selected from the group consisting of a phenyl group, a naphthyl group, a biphenyl group, a terphenyl group, an anthracenyl group, a fluorenyl group, and a pyrenyl group; an unsubstituted $C_3$-$C_{60}$ heteroaryl group; an unsubstituted $C_5$-$C_{50}$ aryl amine group; a substituted monocyclic to tetracyclic aryl group selected from the group consisting of a phenyl group, a naphthyl group, a biphenyl group, a terphenyl group, an anthracenyl group, a fluorenyl group, and a pyrenyl group which is substituted with a $C_1$-$C_5$ alkyl group, a $C_1$-$C_5$ alkoxy group, a cyano group, an amine group, a phenoxy group, a phenyl group or a halogen group; a substituted $C_3$-$C_{60}$ heteroaryl group which is substituted with a $C_1$-$C_5$ alkyl group, a $C_1$-$C_5$ alkoxy group, a cyano group, an amine group, a phenoxy group, a phenyl group, a halogen group or a $C_3$-$C_{10}$ heteroaryl group; or a substituted $C_5$-$C_{50}$ arylamine group which is substituted with a $C_1$-$C_5$ alkyl group, a $C_1$-$C_5$ alkoxy group, a cyano group, an amine group, a phenoxy group, a phenyl group or a halogen group; and $R_4$, $R_5$, $R_7$, $R_8$ and $R_9$ is each independently a hydrogen or a deuterium.

2. A compound of one of the compounds below:

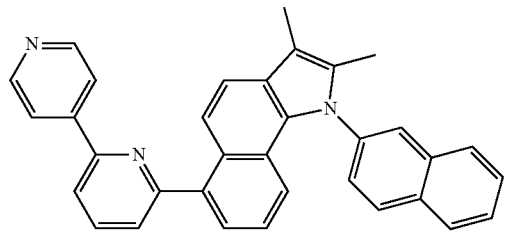

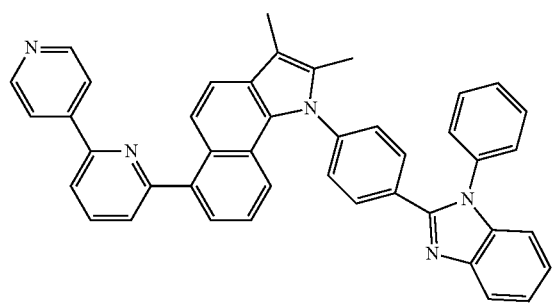

27
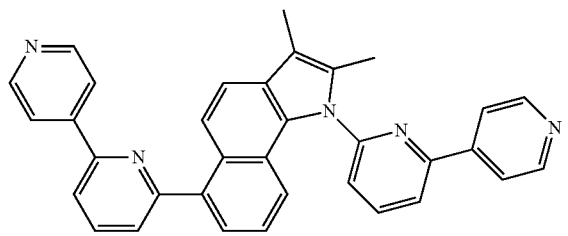
40
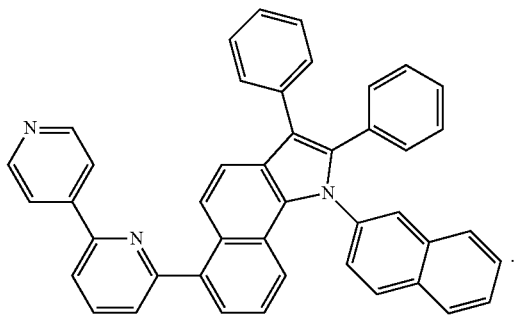
3. A compound of one of the compounds below:
1
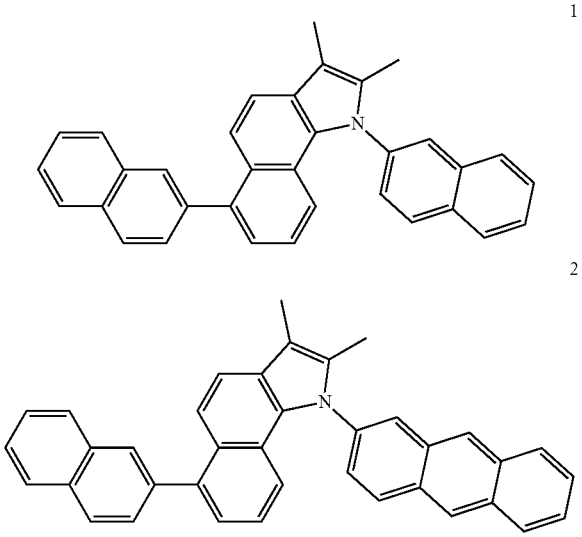
2
3
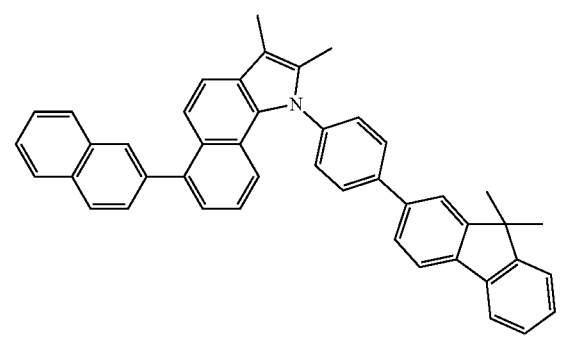
4
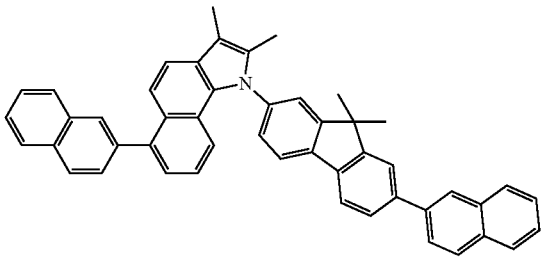
5
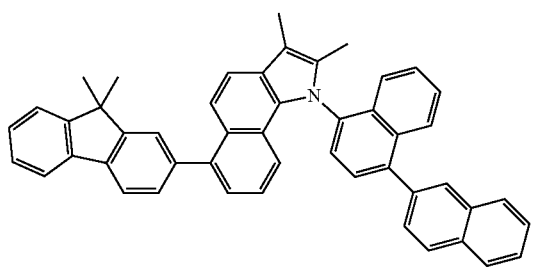
6
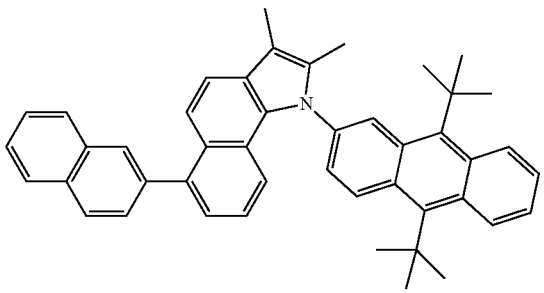
7
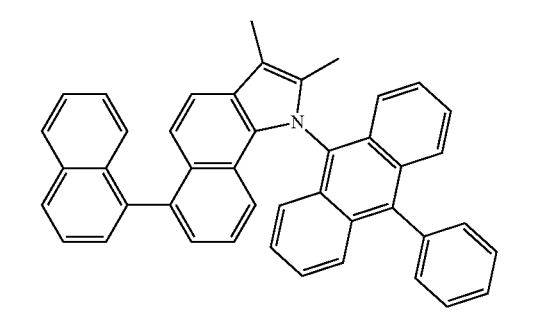
8
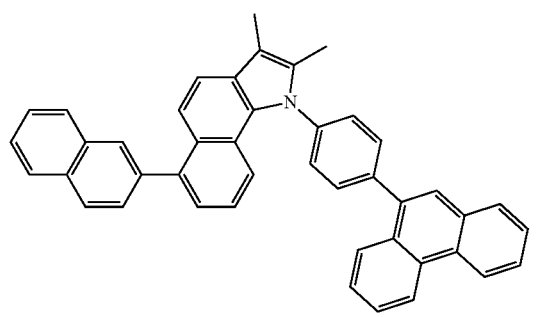

9
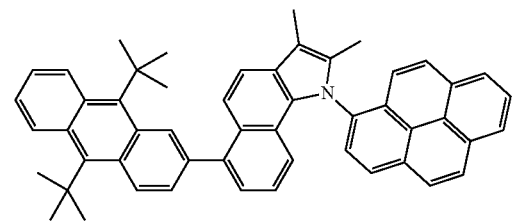
10
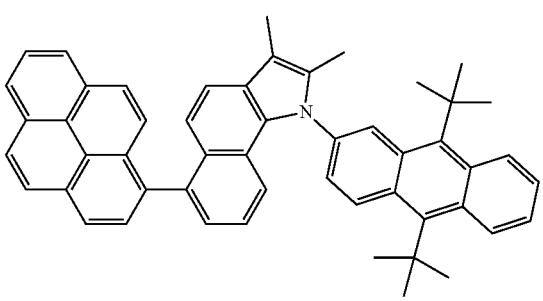
11
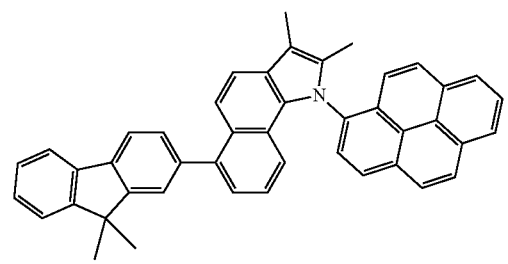
12
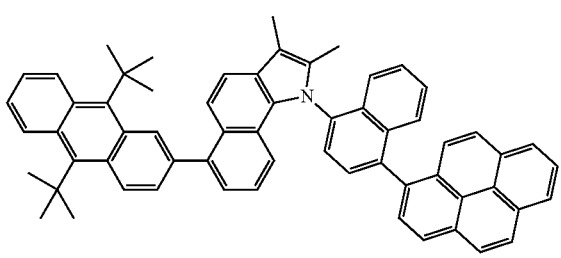
13
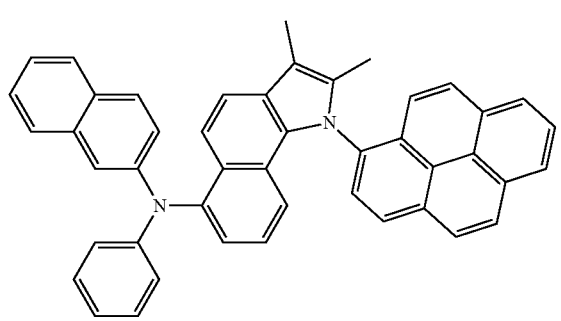
14
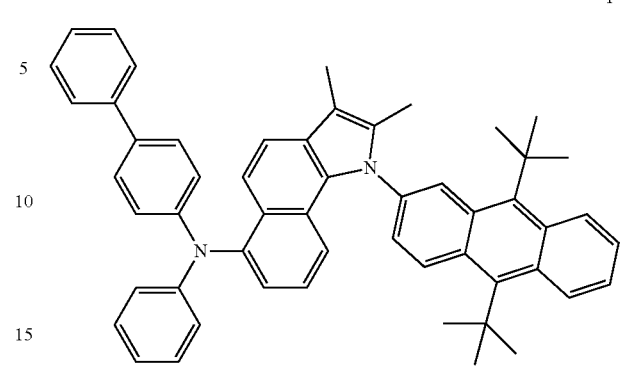
15
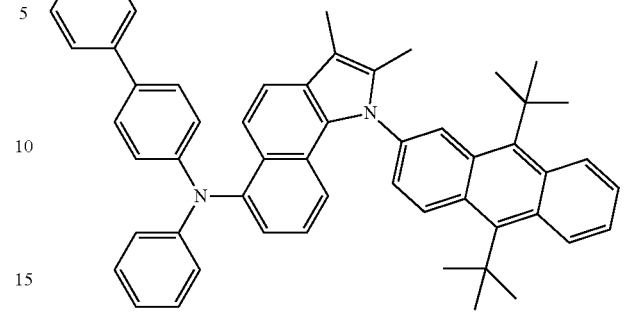
16
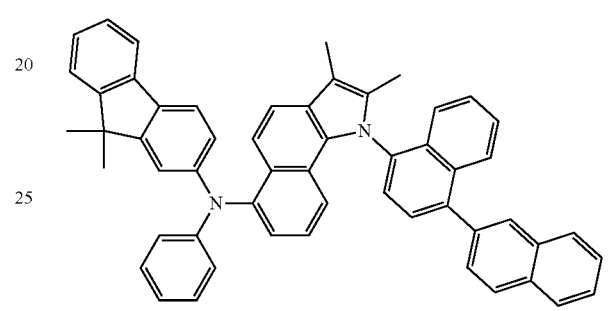
17
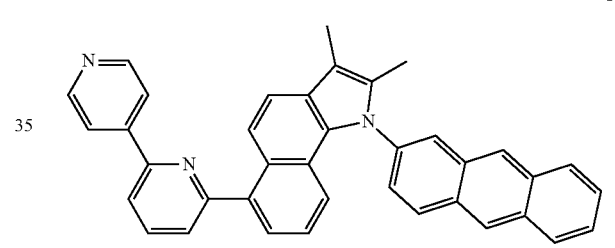
18
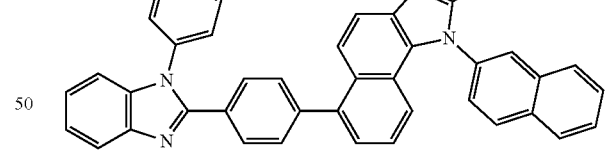

19
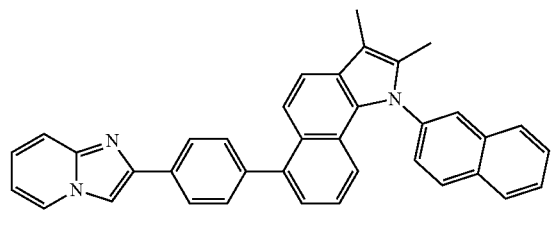
20
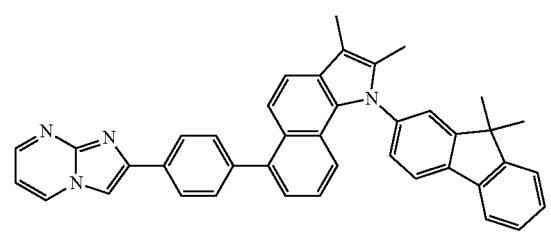
21
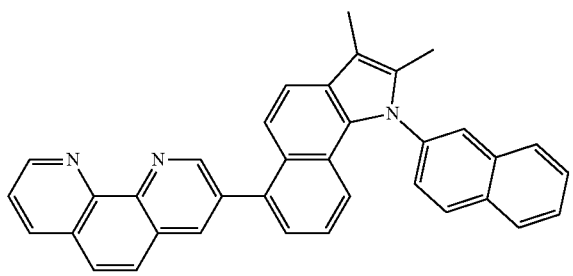
22
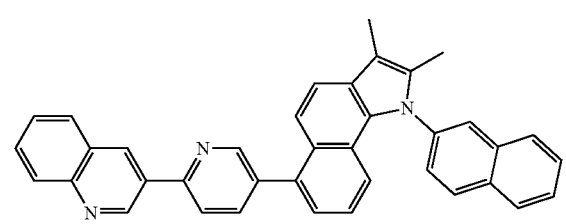
23
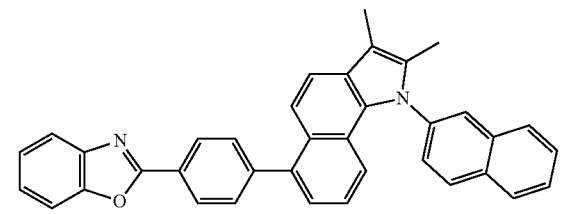
24
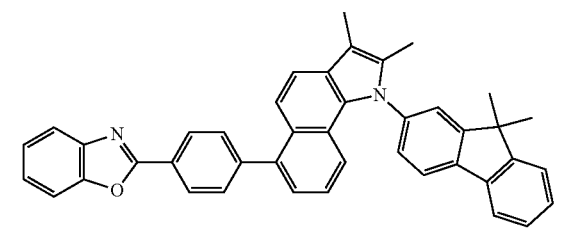
25
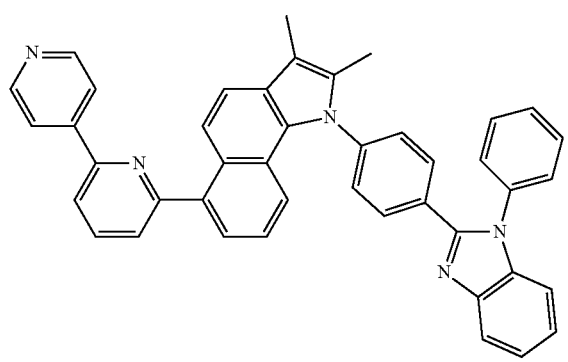
26
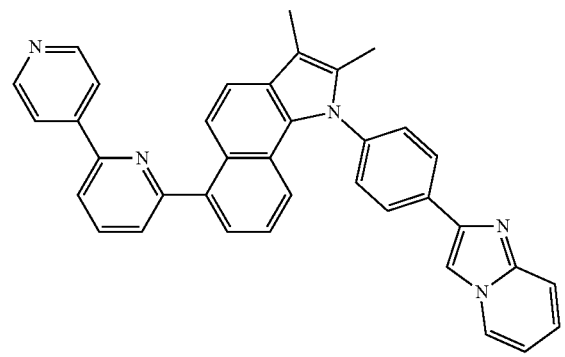
27
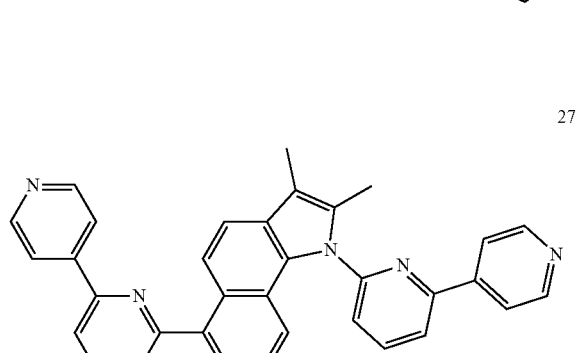
28
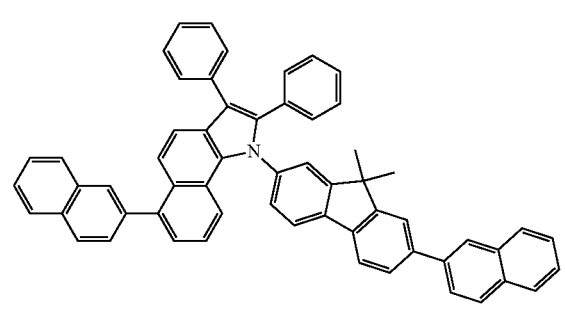

29
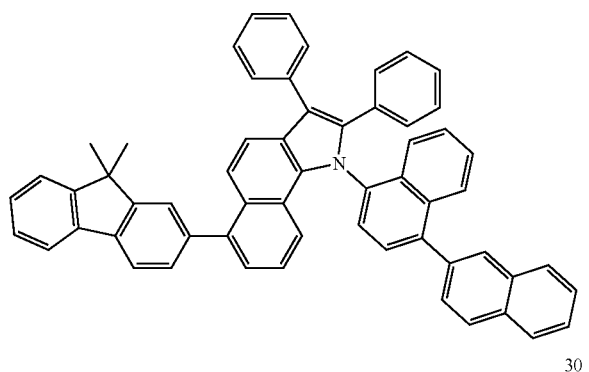
30
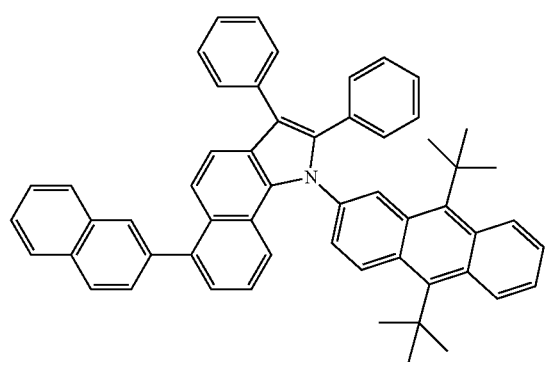
31
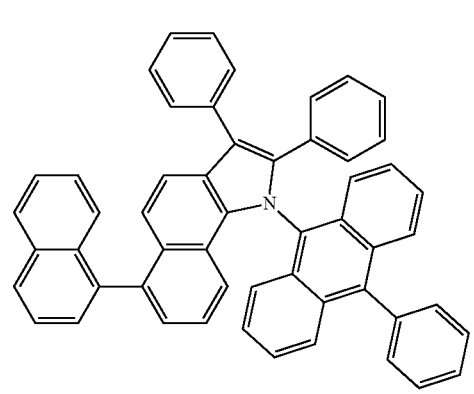
32
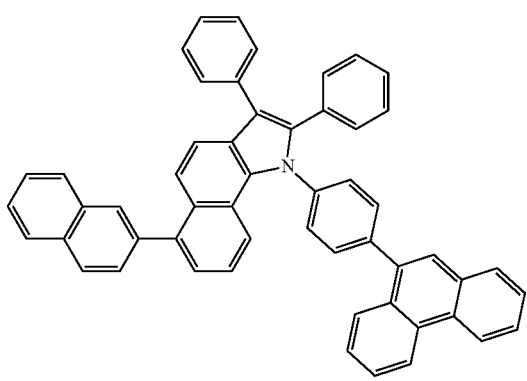
33
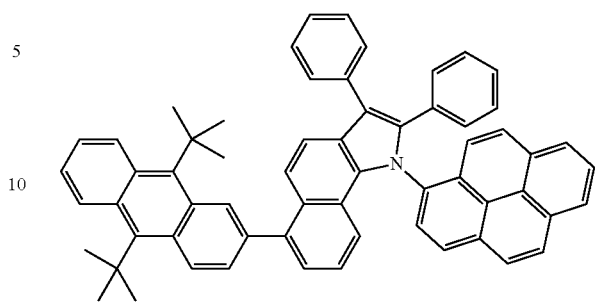
34
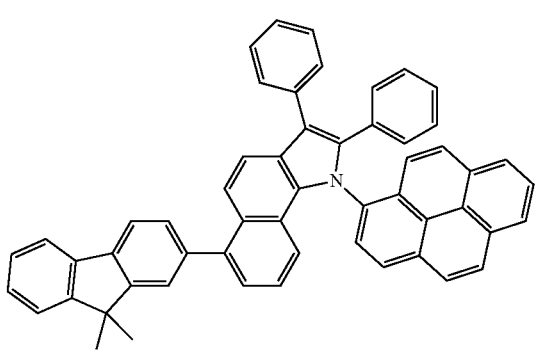
35
36
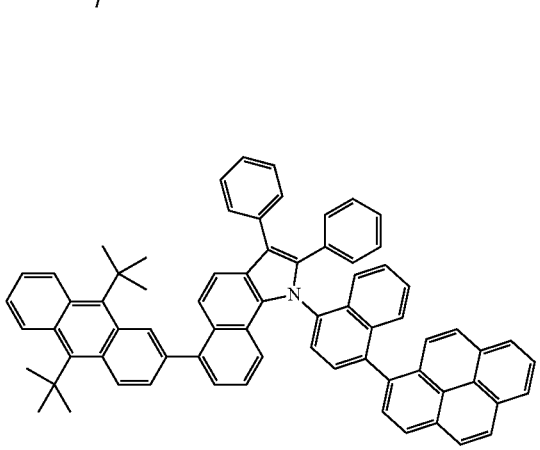

37
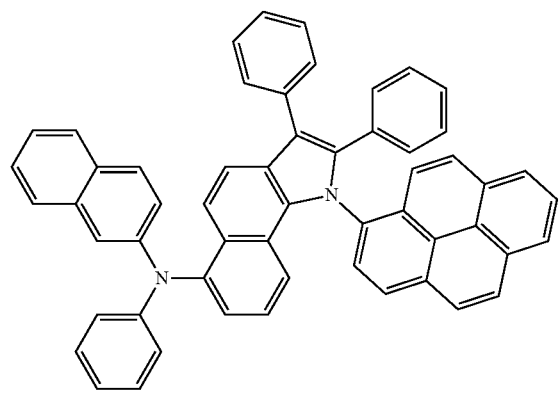
38
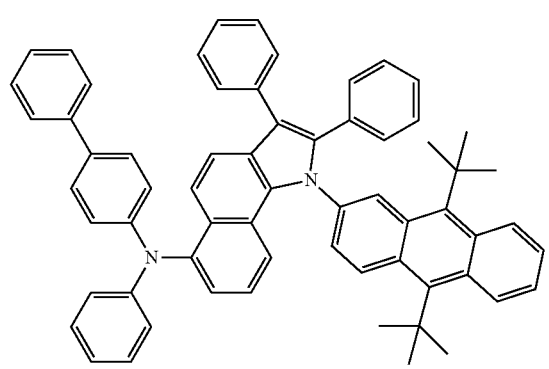
39
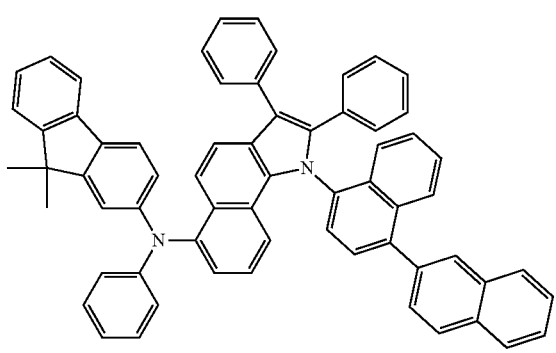
40
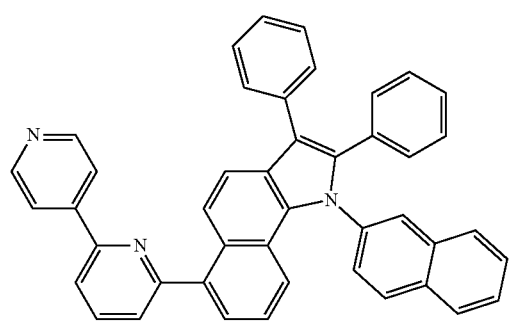
41
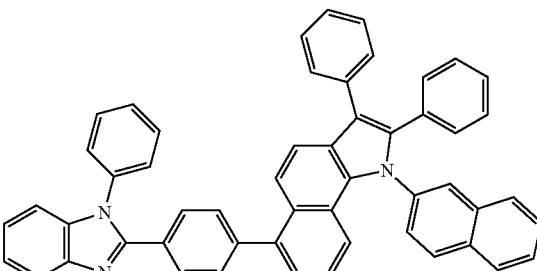
42
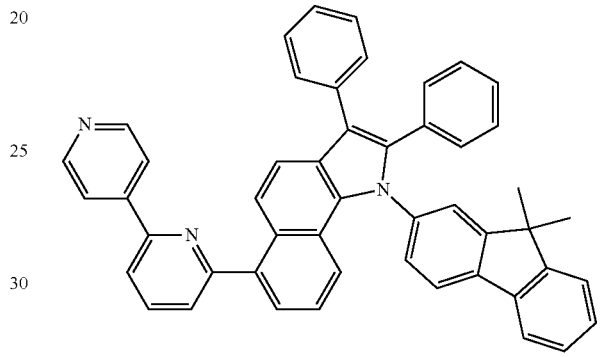
43
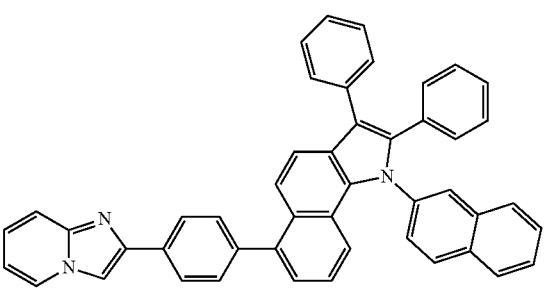
44
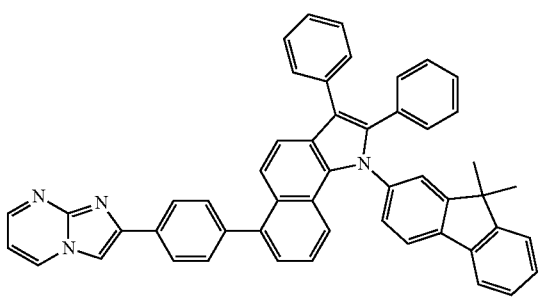

44
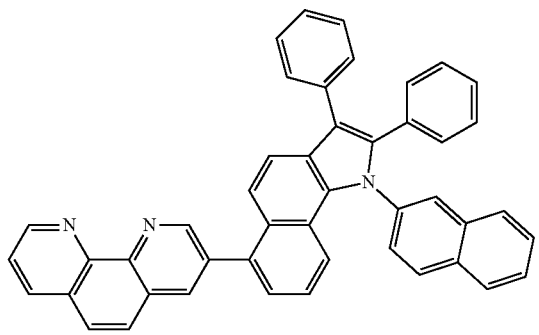
45
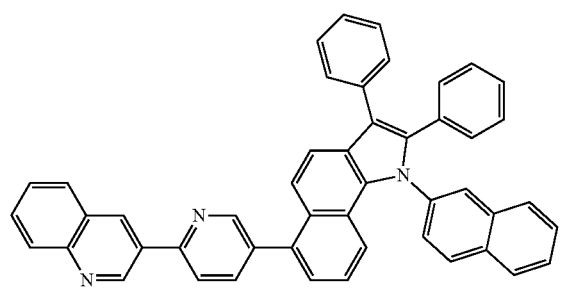
46
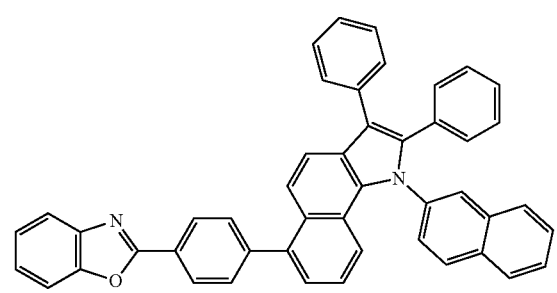
47
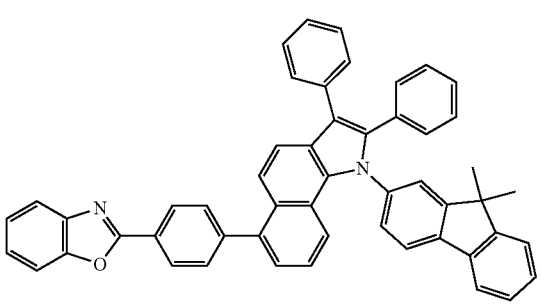
48
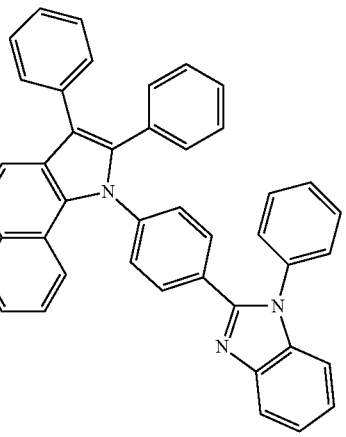
49
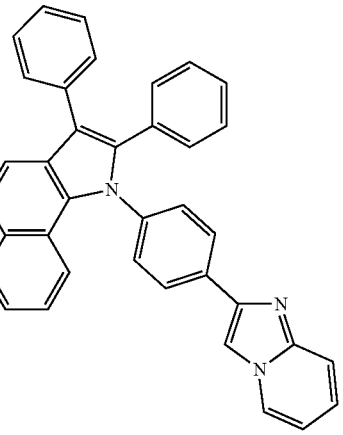
50
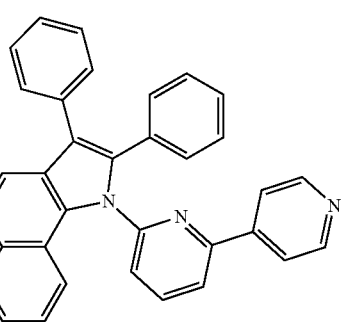
51
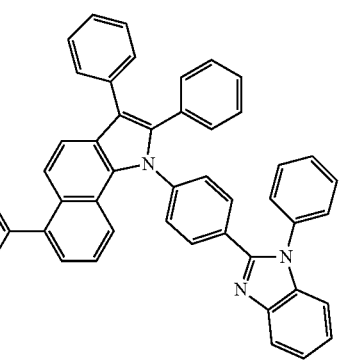

52

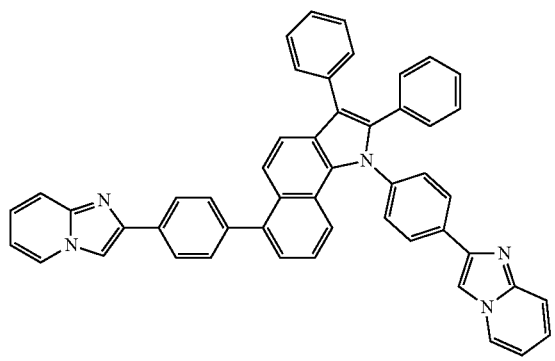

53

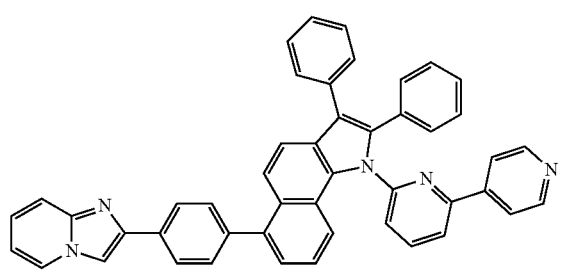

53

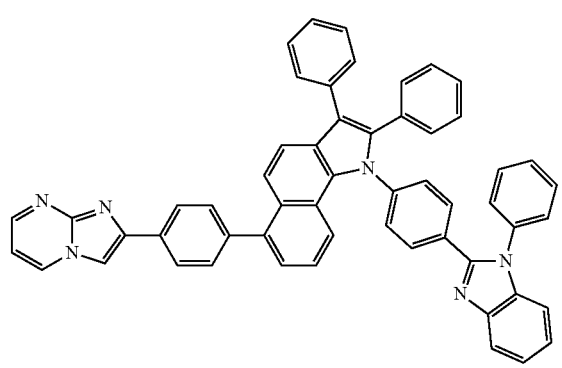

54

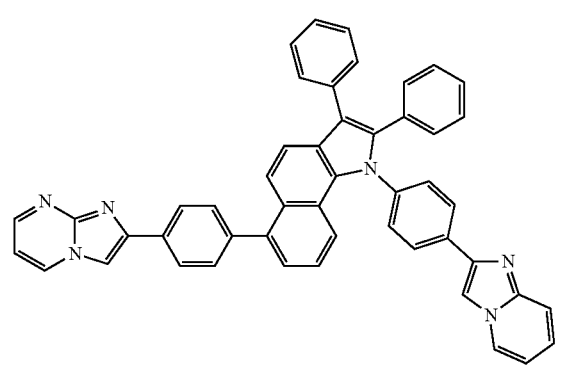

55

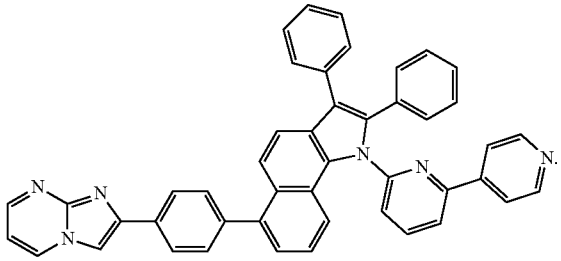

4. An organic light-emitting device comprising:
a first electrode;
a second electrode; and
an organic layer between the first electrode and the second electrode,
wherein the organic layer comprises a first layer including the heterocyclic compound of claim 1.

5. The organic light-emitting device of claim 4, wherein the first layer comprises an electron injection layer, an electron transport layer, or a single layer having both an electron injection function and an electron transport function.

6. The organic light-emitting device of claim 4, wherein the first layer comprises an emission layer.

7. The organic light-emitting device of claim 4, wherein the first layer comprises an emission layer, and the heterocylic compound is a host or a dopant for a fluorescent or phosphorescent device.

8. The organic light-emitting device of claim 4, wherein the organic layer comprises an emission layer, an electron injection layer or an electron transport layer, and the emission layer comprises an anthracene compound, an aryl amine compound, or a styryl compound.

9. The organic light-emitting device of claim 4, wherein the organic layer comprises an emission layer, an electron injection layer or an electron transport layer, and the emission layer comprises a red emission layer, a green emission layer, a blue emission layer or a white emission layer that comprises a phosphorescent compound.

10. The organic light-emitting device of claim 4, wherein the organic layer further comprises a hole injection layer, a hole transport layer, a functional layer having both hole injection and transport functions, an electron blocking layer, an emission layer, a hole blocking layer, an electron transport layer, an electron injection layer and a combination of at least two of these layers.

11. The organic light-emitting device of claim 10, wherein at least one of the hole injection layer, the hole transport layer, and the functional layer having both hole injection and transport functions further comprises a charge-generating material.

12. The organic light-emitting device of claim 9, wherein the electron transport layer comprises an electron transporting organic material and a metal-containing material.

13. The organic light-emitting device of claim 12, wherein the metal-containing material comprises a lithium complex.

14. The organic light-emitting device of claim 4, having a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport structure layer/electron injection layer/second electrode structure.

15. The organic light-emitting device of claim 4, wherein the first layer is formed using a wet process.

16. A flat panel display device comprising the organic light-emitting device of claim 4, wherein the first electrode of the organic light-emitting device is electrically connected to a source electrode or a drain electrode of a thin-film transistor.

* * * * *